US011000076B2

(12) United States Patent
Tremblay

(10) Patent No.: US 11,000,076 B2
(45) Date of Patent: May 11, 2021

(54) ELECTRONIC VAPING DEVICE

(71) Applicant: Martin Tremblay, Montreal (CA)

(72) Inventor: Martin Tremblay, Montreal (CA)

( * ) Notice: Subject to any disclaimer, the term of this patent is extended or adjusted under 35 U.S.C. 154(b) by 0 days.

(21) Appl. No.: 16/571,082

(22) Filed: Sep. 14, 2019

(65) Prior Publication Data
US 2020/0008481 A1      Jan. 9, 2020

Related U.S. Application Data

(63) Continuation of application No. 16/008,009, filed on Jun. 13, 2018, now Pat. No. 10,440,999, which is a continuation of application No. 14/587,117, filed on Dec. 31, 2014, now abandoned.

(60) Provisional application No. 62/035,436, filed on Aug. 10, 2014, provisional application No. 61/922,091, filed on Dec. 31, 2013.

(51) Int. Cl.
    *A24F 47/00* (2020.01)
(52) U.S. Cl.
    CPC .................................. *A24F 47/008* (2013.01)
(58) Field of Classification Search
    CPC .............................. A24F 40/50; A24F 47/008
    See application file for complete search history.

(56) References Cited

U.S. PATENT DOCUMENTS

| | | | | |
|---|---|---|---|---|
| 2007/0061881 A1* | 3/2007 | Eyre | ...................... | G06Q 30/02 726/21 |
| 2008/0295151 A1* | 11/2008 | Xia | ......................... | G06Q 30/02 726/2 |
| 2013/0220315 A1* | 8/2013 | Conley | ................ | H05B 1/0244 128/202.21 |
| 2013/0284192 A1* | 10/2013 | Peleg | ..................... | A24F 47/004 131/329 |
| 2014/0013116 A1* | 1/2014 | Smith | ................... | H04W 12/06 713/168 |
| 2015/0026798 A1* | 1/2015 | Huang | .................... | G06F 21/32 726/19 |
| 2015/0114407 A1* | 4/2015 | Duncan | ................. | A24F 47/002 131/329 |
| 2016/0081393 A1* | 3/2016 | Black | ................... | H05B 1/0252 392/387 |
| 2016/0200463 A1* | 7/2016 | Hodges | ............... | G07F 17/0092 53/415 |

* cited by examiner

*Primary Examiner* — Eric Yaary

(57) ABSTRACT

An electronic vaping device may be designed to enhance or facilitate its use. For example, the electronic vaping device may: allow a capability of the electronic vaping device to provide vapor to be altered (e.g., disabled, reduced, enabled, or increased) in some situations (e.g., to prevent unauthorized vaping by a child, teenager or other individual); be able to communicate with an external communication device (e.g., a smartphone, a computer, etc.) to convey a notification of potential unauthorized use of the electronic vaping device (e.g., by a child, teenager or other unauthorized user); implement a physical deterrent to its unauthorized use; be able to visually convey information (e.g., advertisements, notifications, etc.); and/or be able to capture images and/or sounds (e.g., record pictures and/or video, speech, music, etc.).

20 Claims, 24 Drawing Sheets

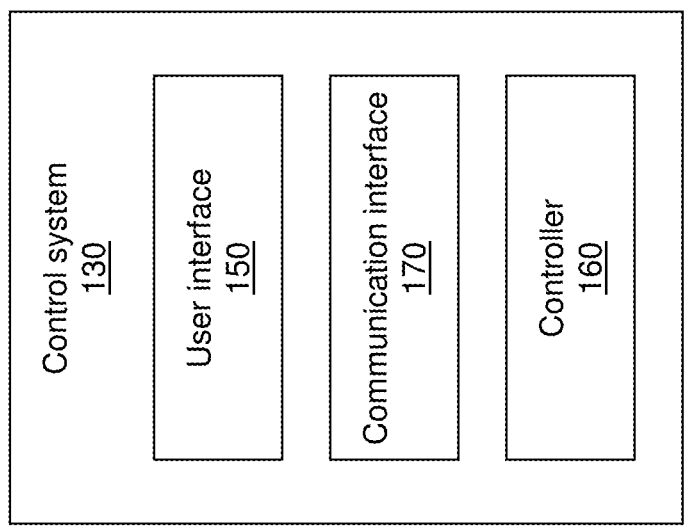

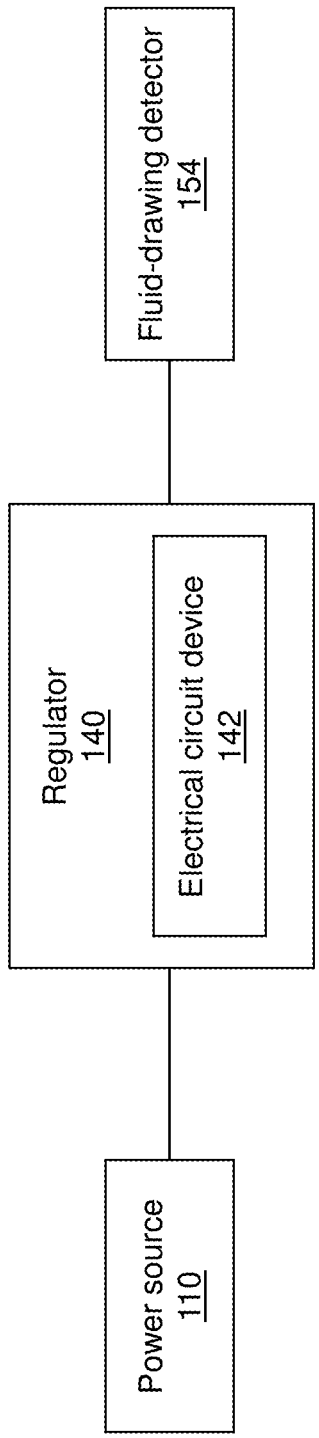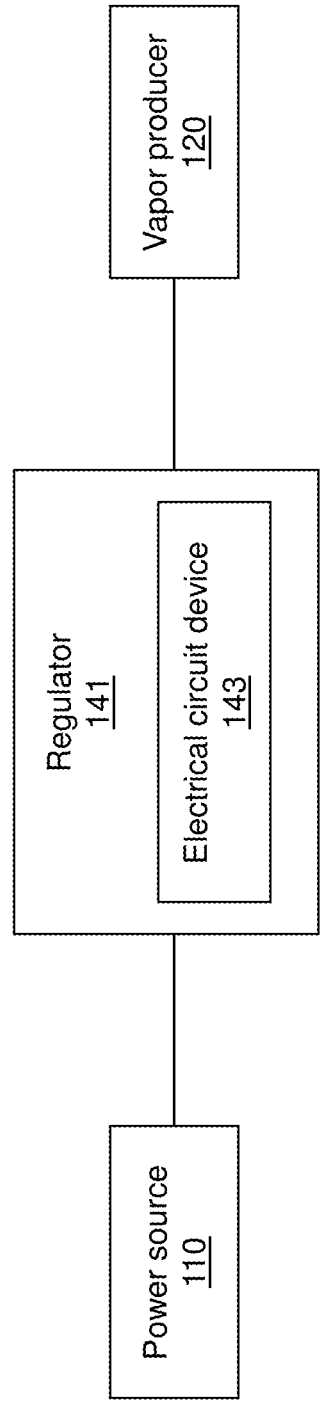

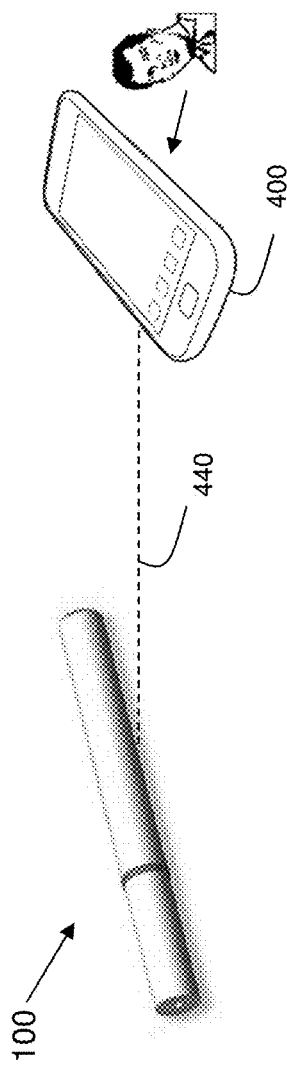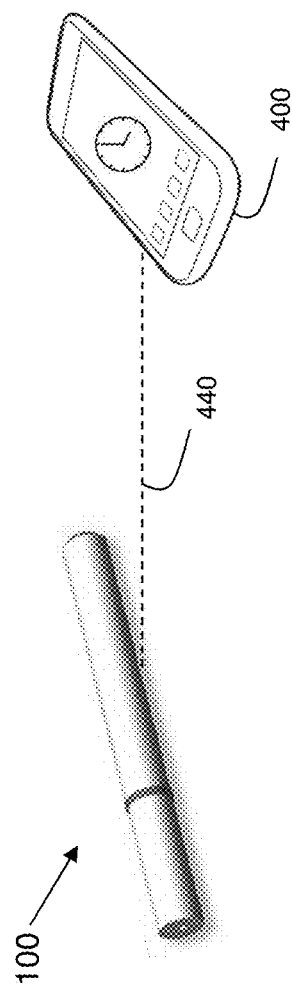

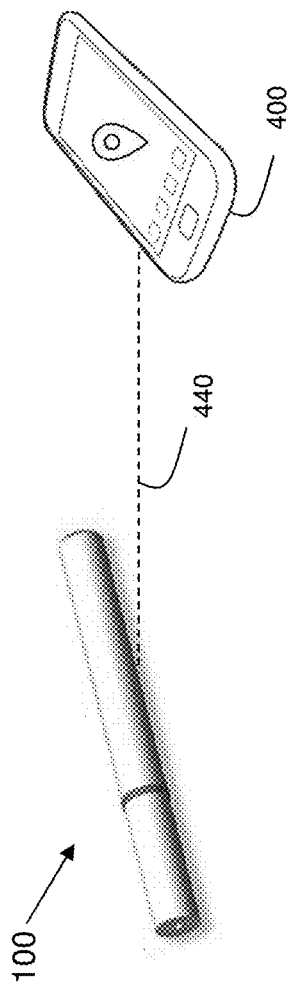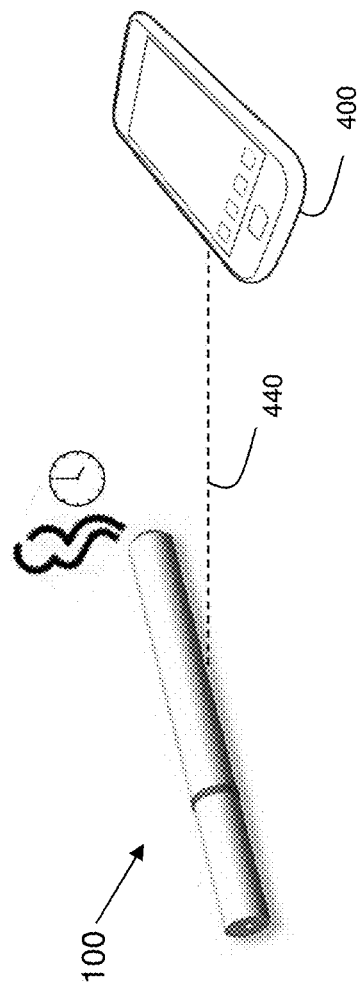

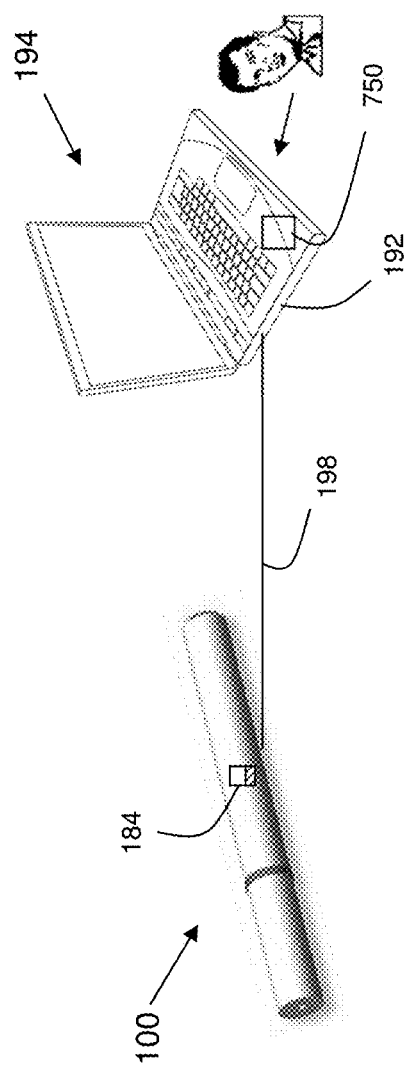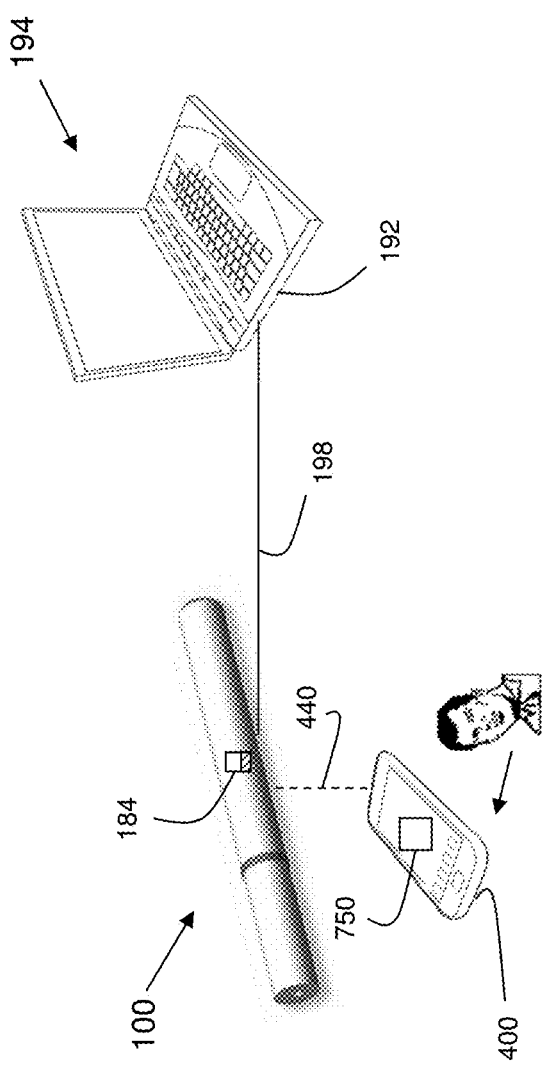
FIG. 24
FIG. 25

US 11,000,076 B2

ELECTRONIC VAPING DEVICE

CROSS-REFERENCE TO RELATED APPLICATIONS

This application is a continuation of U.S. patent application Ser. No. 16/008,009 filed on Jun. 13, 2018, which is a continuation of U.S. patent application Ser. No. 14/587,117 filed on Dec. 31, 2014, and claims the benefit under 35 USC 119(e) of U.S. Provisional Patent Application 61/922,091 filed on Dec. 31, 2013 and U.S. Provisional Patent Application filed on 62/035,436 filed on Aug. 10, 2014, all of which are hereby incorporated by reference herein.

FIELD

The invention relates to electronic vaping devices usable by users to "vape", i.e., draw (e.g., inhale, puff, etc.) vapor from the electronic vaping devices using their mouth.

BACKGROUND

Electronic vaping devices, which are sometimes referred to as "electronic cigarettes", "e-cigarettes" or "personal vaporizers", are becoming increasingly popular. For instance, electronic cigarettes may be used by various people to simulate smoking (e.g., tobacco smoking), including current or past smokers of tobacco cigarettes (e.g., who are trying to quit or may have previously quit tobacco smoking) and individuals who never were smokers of tobacco cigarettes.

While they are certainly useful to various people, electronic cigarettes may sometimes bring about some additional considerations. For example, in some cases, it may undesirable for certain persons to readily use electronic cigarettes, such as a child or teenager who may not be allowed to vape or someone who may have stolen or found an electronic cigarette belonging to somebody else. As another example, in some situations, it may be undesirable for electronic cigarettes to be vaped at certain places and/or times.

As yet another example, in some cases, it may be desirable for an electronic cigarette to be useful for purposes other than vaping.

For these and/or other reasons, there is a need for improvements directed to electronic vaping devices.

SUMMARY

In various embodiments of the invention, an electronic vaping device may be designed to enhance or facilitate its use. For example, in some embodiments, the electronic vaping device may: allow a capability of the electronic vaping device to provide vapor to be altered (e.g., disabled, reduced, enabled, or increased) in some situations (e.g., to prevent unauthorized vaping by a child, teenager or other individual); be able to communicate with an external communication device (e.g., a smartphone, a computer, etc.) to convey a notification of potential unauthorized use of the electronic vaping device (e.g., by a child, teenager or other unauthorized user); implement a physical deterrent to its unauthorized use; be able to visually convey information (e.g., advertisements, notifications, etc.); and/or be able to capture images and/or sounds (e.g., record pictures and/or video, speech, music, etc.).

For example, according to an aspect of the invention, there is provided an electronic vaping device. The electronic vaping device comprises: an outlet; a vapor producer configured to produce vapor drawable by a user through the outlet using the user's mouth; and a controller configured to cause a capability of the electronic vaping device to provide vapor through the outlet to be altered in response to a condition being met.

According to another aspect of the invention, there is provided a method for controlling an electronic vaping device. The electronic vaping device comprises an outlet and a vapor producer configured to produce vapor drawable by a user through the outlet using the user's mouth. The method comprises: determining that a condition is met; and causing a capability of the electronic vaping device to provide vapor through the outlet to be altered in response to the condition being met.

According to another aspect of the invention, there is provided an apparatus for controlling an electronic vaping device. The electronic vaping device comprises an outlet and a vapor producer configured to produce vapor drawable by a user through the outlet using the user's mouth. The apparatus comprises a memory portion and a processing portion which is configured to: determine that a condition is met; and cause a capability of the electronic vaping device to provide vapor through the outlet to be altered in response to the condition being met.

According to another aspect of the invention, there is provided a computer-readable storage medium storing instructions which, when executed by a computing entity, cause the computing entity to implement a method for controlling an electronic vaping device. The electronic vaping device comprises an outlet and a vapor producer configured to produce vapor drawable by a user through the outlet using the user's mouth. The method comprises: determining that a condition is met; and causing a capability of the electronic vaping device to provide vapor through the outlet to be altered in response to the condition being met.

According to another aspect of the invention, there is provided an electronic vaping device. The electronic vaping device comprises: an outlet; a vapor producer configured to produce vapor drawable by a user through the outlet using the user's mouth; and a controller configured to cause a capability of the electronic vaping device to provide vapor through the outlet to be disabled in response to an event other than a manual shutdown of the electronic vaping device.

According to another aspect of the invention, there is provided a method for controlling an electronic vaping device. The electronic vaping device comprises an outlet and a vapor producer configured to produce vapor drawable by a user through the outlet using the user's mouth. The method comprises: determining that an event other than a manual shutdown of the electronic vaping device occurred; and causing a capability of the electronic vaping device to provide vapor through the outlet to be disabled in response to the event.

According to another aspect of the invention, there is provided an apparatus for controlling an electronic vaping device. The electronic vaping device comprises an outlet and a vapor producer configured to produce vapor drawable by a user through the outlet using the user's mouth. The apparatus comprises a memory portion and a processing portion which is configured to: determine that an event other than a manual shutdown of the electronic vaping device occurred; and cause a capability of the electronic vaping device to provide vapor through the outlet to be disabled in response to the event.

According to another aspect of the invention, there is provided a computer-readable storage medium storing instructions which, when executed by a computing entity, cause the computing entity to implement a method for controlling an electronic vaping device.

The electronic vaping device comprises an outlet and a vapor producer configured to produce vapor drawable by a user through the outlet using the user's mouth. The method comprises: determining that an event other than a manual shutdown of the electronic vaping device occurred; and causing a capability of the electronic vaping device to provide vapor through the outlet to be disabled in response to the event.

According to another aspect of the invention, there is provided an electronic vaping device. The electronic vaping device comprises: an outlet; a vapor producer configured to produce vapor drawable by a user through the outlet using the user's mouth; and a controller configured to cause a capability of the electronic vaping device to provide vapor through the outlet to be disabled in response to an external command from a communication device that is external to the electronic vaping device.

According to another aspect of the invention, there is provided a method for controlling an electronic vaping device. The electronic vaping device comprises an outlet and a vapor producer configured to produce vapor drawable by a user through the outlet using the user's mouth. The method comprises: receiving an external command from a communication device that is external to the electronic vaping device; and causing a capability of the electronic vaping device to provide vapor through the outlet to be disabled in response to the external command.

According to another aspect of the invention, there is provided an apparatus for controlling an electronic vaping device. The electronic vaping device comprises an outlet and a vapor producer configured to produce vapor drawable by a user through the outlet using the user's mouth. The apparatus comprises a memory portion and a processing portion which is configured to: receive an external command from a communication device that is external to the electronic vaping device; and cause a capability of the electronic vaping device to provide vapor through the outlet to be disabled in response to the external command.

According to another aspect of the invention, there is provided a computer-readable storage medium storing instructions which, when executed by a computing entity, cause the computing entity to implement a method for controlling an electronic vaping device. The electronic vaping device comprises an outlet and a vapor producer configured to produce vapor drawable by a user through the outlet using the user's mouth. The method comprises: receiving an external command from a communication device that is external to the electronic vaping device; and causing a capability of the electronic vaping device to provide vapor through the outlet to be disabled in response to the external command.

According to another aspect of the invention, there is provided an electronic vaping device. The electronic vaping device comprises: an outlet; a vapor producer configured to produce vapor drawable by a user through the outlet using the user's mouth; and a controller configured to cause a capability of the electronic vaping device to provide vapor through the outlet to be altered in response to a condition independent of user input being met.

According to another aspect of the invention, there is provided a method for controlling an electronic vaping device. The electronic vaping device comprises an outlet and a vapor producer configured to produce vapor drawable by a user through the outlet using the user's mouth. The method comprises: determining that a condition independent of user input is met; and causing a capability of the electronic vaping device to provide vapor through the outlet to be altered in response to the condition independent of user input being met.

According to another aspect of the invention, there is provided an apparatus for controlling an electronic vaping device. The electronic vaping device comprises an outlet and a vapor producer configured to produce vapor drawable by a user through the outlet using the user's mouth. The apparatus comprises a memory portion and a processing portion which is configured to: determine that a condition independent of user input is met; and cause a capability of the electronic vaping device to provide vapor through the outlet to be altered in response to the condition independent of user input being met.

According to another aspect of the invention, there is provided a computer-readable storage medium storing instructions which, when executed by a computing entity, cause the computing entity to implement a method for controlling an electronic vaping device. The electronic vaping device comprises an outlet and a vapor producer configured to produce vapor drawable by a user through the outlet using the user's mouth. The method comprises: determining that a condition independent of user input is met; and causing a capability of the electronic vaping device to provide vapor through the outlet to be altered in response to the condition independent of user input being met.

According to another aspect of the invention, there is provided an apparatus for controlling an electronic vaping device. The electronic vaping device comprises an outlet and a vapor producer configured to produce vapor drawable by a user through the outlet using the user's mouth. The apparatus comprises a memory portion and a processing portion which is configured to: determine that a condition is met; and in response to the condition being met, issuing a command to the electronic vaping device to alter a capability of the electronic vaping device to provide vapor through the outlet.

According to another aspect of the invention, there is provided a computer-readable storage medium storing instructions which, when executed by a computing entity, cause the computing entity to implement a method for controlling an electronic vaping device. The electronic vaping device comprises an outlet and a vapor producer configured to produce vapor drawable by a user through the outlet using the user's mouth. The method comprises: determining that a condition is met; and in response to the condition being met, issuing a command to the electronic vaping device to alter a capability of the electronic vaping device to provide vapor through the outlet.

According to another aspect of the invention, there is provided a communication device for interacting with an electronic vaping device over a communication link. The electronic vaping device comprises an outlet and a vapor producer configured to produce vapor drawable by a user through the outlet using the user's mouth. The communication device comprises a memory portion and a processing portion which is configured to: determine that a condition is met; and in response to the condition being met, transmitting a command to the electronic vaping device via the communication link to alter a capability of the electronic vaping device to provide vapor through the outlet.

According to another aspect of the invention, there is provided a method for controlling an electronic vaping device. The electronic vaping device comprises an outlet and a vapor producer configured to produce vapor drawable by a user through the outlet using the user's mouth. The method comprises: determining that a condition is met; and in response to the condition being met, issuing a command to the electronic vaping device to alter a capability of the electronic vaping device to provide vapor through the outlet.

According to another aspect of the invention, there is provided an apparatus for controlling an electronic vaping device. The electronic vaping device comprises an outlet and a vapor producer configured to produce vapor drawable by a user through the outlet using the user's mouth. The apparatus comprises a memory portion and a processing portion which is configured to: receive first data indicative of a user's desire to enable vaping of the electronic vaping device; verify whether authorization criteria are met; and in case the authorization criteria are met, send second data over a communication link to enable vaping of the electronic vaping device.

According to another aspect of the invention, there is provided a computer-readable storage medium storing instructions which, when executed by a computing entity, cause the computing entity to implement a method for controlling an electronic vaping device. The electronic vaping device comprises an outlet and a vapor producer configured to produce vapor drawable by a user through the outlet using the user's mouth. The method comprises: receiving first data indicative of a user's desire to enable vaping of the electronic vaping device; verifying whether authorization criteria are met; and in case the authorization criteria are met, sending second data over a communication link to enable vaping of the electronic vaping device.

According to another aspect of the invention, there is provided a method for controlling an electronic vaping device. The electronic vaping device comprises an outlet and a vapor producer configured to produce vapor drawable by a user through the outlet using the user's mouth. The method comprises: receiving first data indicative of a user's desire to enable vaping of the electronic vaping device; verifying whether authorization criteria are met; and in case the authorization criteria are met, sending second data over a communication link to enable vaping of the electronic vaping device.

According to another aspect of the invention, there is provided an apparatus for controlling an electronic vaping device. The electronic vaping device comprises an outlet and a vapor producer configured to produce vapor drawable by a user through the outlet using the user's mouth. The apparatus comprises a memory portion and a processing portion which is configured to: detect potential unauthorized use of the electronic vaping device; and cause a notification to be issued in response to the potential unauthorized use of the electronic vaping device.

According to another aspect of the invention, there is provided a computer-readable storage medium storing instructions which, when executed by a computing entity, cause the computing entity to implement a method for controlling an electronic vaping device. The electronic vaping device comprises an outlet and a vapor producer configured to produce vapor drawable by a user through the outlet using the user's mouth. The method comprises: detecting potential unauthorized use of the electronic vaping device; and causing a notification to be issued in response to the detecting.

According to another aspect of the invention, there is provided a method for controlling an electronic vaping device. The electronic vaping device comprises an outlet and a vapor producer configured to produce vapor drawable by a user through the outlet using the user's mouth. The method comprises: detecting potential unauthorized use of the electronic vaping device; and causing a notification to be issued in response to the detecting.

According to another aspect of the invention, there is provided an electronic vaping device. The electronic vaping device comprises: an outlet; a vapor producer configured to produce vapor drawable by a user through the outlet using the user's mouth; and a visual output device configured to visually convey information.

According to another aspect of the invention, there is provided an electronic vaping device. The electronic vaping device comprises: an outlet; a vapor producer configured to produce vapor drawable by a user through the outlet using the user's mouth; and a media-capturing device configured to capture media.

According to another aspect of the invention, there is provided an electronic vaping device. The electronic vaping device comprises an outlet and a vapor producer configured to produce vapor drawable by a user through the outlet using the user's mouth. The electronic vaping device implements a physical deterrent to unauthorized use of the electronic vaping device.

These and other aspects of the invention will now become apparent to those of ordinary skill in the art upon review of the following description of embodiments of the invention in conjunction with the accompanying drawings.

BRIEF DESCRIPTION OF THE DRAWINGS

A detailed description of embodiments of the invention is provided below, by way of example only, with reference to the accompanying drawings, in which:

FIGS. 3 to 6 show examples of components of the electronic vaping device;

FIGS. 8 to 10 show examples of components of the electronic vaping device to alter a vapor-providing capability of the electronic vaping device;

FIGS. 12 to 28 show various examples of embodiments in which the vapor-providing capability of the electronic vaping device can be altered;

Figure 2:
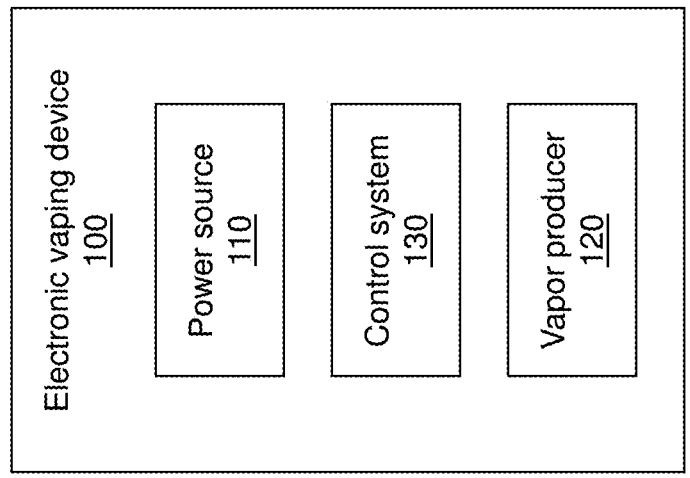
FIGS. 1 and 2 show an example of an electronic vaping device in accordance with an embodiment of the invention.
Figure 1:
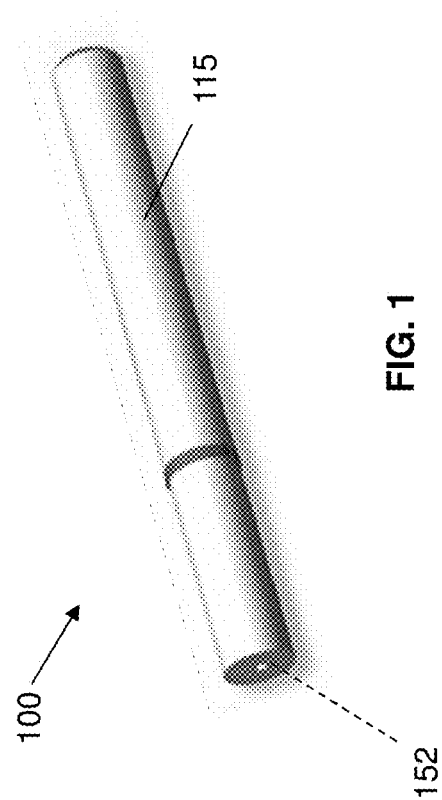
Figure 4:
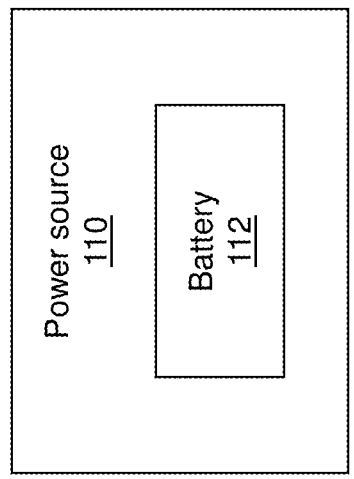
Figure 3:
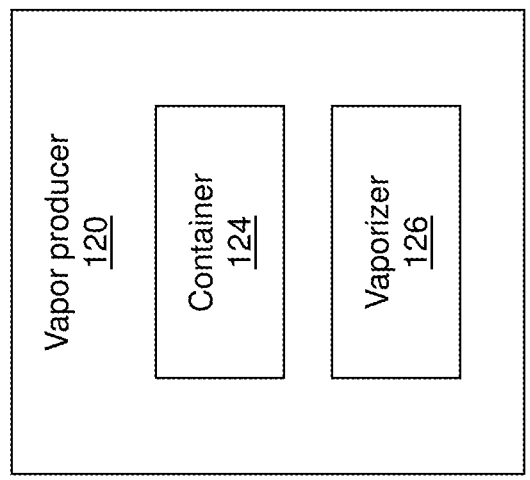

It is to be expressly understood that the description and drawings are only for the purpose of illustrating certain embodiments of the invention and are an aid for understanding. They are not intended to be a definition of the limits of the invention.

DETAILED DESCRIPTION OF EMBODIMENTS

FIGS. 1 to 5 show an example of an electronic vaping device 100 in accordance with an embodiment of the invention. The electronic vaping device 100, which may be referred to as an "electronic cigarette", "e-cigarette", or "personal vaporizer", is usable by a user to "vape", i.e., draw (e.g., inhale, puff, etc.) vapor through an outlet 152 of the electronic vaping device 100 using his/her mouth, such as, for instance, to simulate smoking (e.g., tobacco smoking). In various cases, the user may inhale the vapor drawn from the electronic cigarette 100 (i.e., inspire the vapor into his/her lungs) or may hold the vapor drawn from the electronic cigarette 100 in his/her mouth and/or throat without necessarily inspiring it into his/her lungs.

The electronic cigarette 100 comprises a housing 115, a power source 110 to supply power for the electronic cigarette 100, a vapor producer 120 configured to produce vapor drawable (e.g., inhalable) by the user through the outlet 152, and a control system 130 to control operation of the electronic cigarette 100.

As further discussed below, in various embodiments, the electronic cigarette 100 may be designed to enhance or facilitate its use, such as, for example, by:
- allowing a capability of the electronic cigarette 100 to provide vapor through the outlet 152 to be altered (e.g., disabled, reduced, enabled, or increased) in some situations (e.g., to prevent unauthorized vaping by a child, teenager or other individual);
- being able to communicate with an external communication device (e.g., a smartphone, a computer, etc.) to convey a notification of potential unauthorized use of the electronic cigarette 100 (e.g., by a child, teenager or other unauthorized user);
- implementing a physical deterrent to its unauthorized use (e.g., by a child, teenager or other unauthorized user)
- being able to visually convey information (e.g., advertisements, notifications, etc.); and/or
- being able to capture images and/or sounds (e.g., record pictures and/or video, speech, music, etc.).

The vapor producer 120 comprises a container 124 to store a substance to provide the vapor drawable (e.g., inhalable) by the user. For example, in this embodiment, the substance includes a liquid that is vaporizable. In some cases, the liquid may contain nicotine. Additionally or alternatively, the liquid may be flavored so that the vapor it produces is flavored. In other embodiments, the container 124 may include dry herbs and/or other non-liquid content, or any other suitable content (e.g., alcohol without liquid (AWOL) (e.g., Vaportini™ manufactured by Vaportini Inc., Chicago, Ill., 60618 or Palcohol™ manufactured by Lipsmark LLC, Tempe, Ariz., 85283)). In some embodiments, the electronic cigarette 100 may be disposable such that it can be discarded after the substance stored in the vapor producer 120 has been completely consumed. Alternatively, in other embodiments, the electronic cigarette 100 may be reusable such that the vapor producer 120 may be replenished with an additional amount of the substance (e.g., in a cartridge) to keep producing vapor.

In addition, in this embodiment, the vapor producer 120 comprises a vaporizer 126, sometimes referred to as an "atomizer", to vaporize the liquid stored in the container 124. To that end, the vaporizer 126 may comprise a heater to heat the liquid for vaporizing it. In other embodiments, a system other than a heater may be used. When combined with a cartridge containing the substance to be vaporized, the atomizer may be referred to as a "cartomizer".

The power source 110 is connected to other components of the electronic cigarette 100, including the vapor producer 120 and the control system 130, to power them. To that end, the power source 110 comprises a battery 112. In some cases, the battery 112 may be rechargeable (e.g., where the electronic cigarette 100 is reusable).

The control system 130 comprises various components to control operation of the electronic cigarette 100, including, in this embodiment, a user interface 150 and a controller 160.

The user interface 150 interfaces with the user in order to process inputs received from the user. For example, the user interface 150 comprises the outlet 152 over which the user can place his/her mouth to vape.

Figure 6:
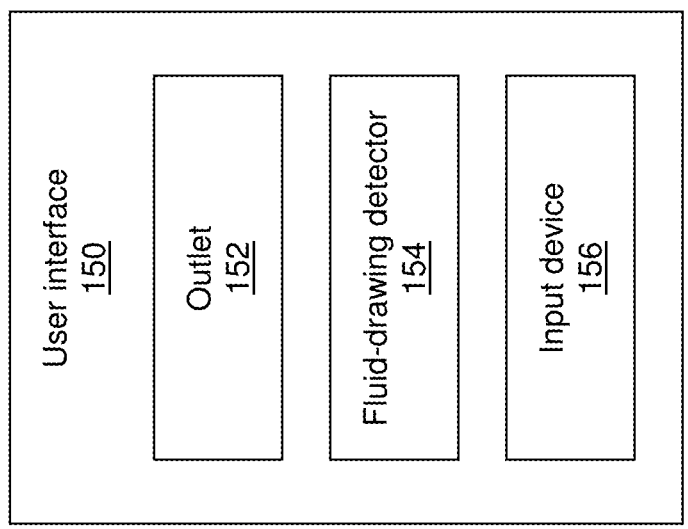

In this embodiment, with additional reference to FIG. 6, the user interface 150 comprises a fluid-drawing detector 154 which detects when the user has drawn (e.g., puffed, inhaled, etc.) fluid through the outlet 152. Fluid that can be drawn (e.g., puffed, inhaled, etc.) though the outlet 152 may include vapor produced by the vapor producer 120 and/or air or another gas or liquid contained within the electronic cigarette 100. For instance, in some cases, the fluid-drawing detector 154, which can sometimes be referred to as an "inhaling detector" even though the user may sometimes merely puff without actually involving the lungs, may comprise a flow sensor (e.g., an airflow sensor) to sense a flow of fluid when the user draws (e.g., puffs, inhales, etc.) the fluid through the outlet 152. The fluid-drawing detector 154 outputs a signal to the controller 160, which processes this signal and consequently activates the vaporizer 126 (e.g., turns on a heater therein). Activation of the vaporizer 126 can be done by issuing a signal (e.g., a "vaporize enable" signal) to the vaporizer 126. The vaporizer 126 responds by vaporizing a portion of the liquid (that may have been drawn from the container 124, e.g., using a wicking material), producing vapor which can be brought into the user's mouth by continuing to draw (e.g., puff, inhale, etc.) through the outlet 152. Should drawing (e.g., puffing, inhaling, etc.) of the vapor cease, this may be detected by the fluid-drawing detector 154 and the controller 160 may responsively control the vaporizer 126 (e.g., by causing the heater to cease heating). The fluid-drawing detector 154 may be at or near the outlet 152, or it may be disposed further along the housing 115, closer to the vaporizer 126.

The user interface 150 may be configured to interact in various additional ways with the user. For example, in some embodiments, the user interface 150 may be configured to process (e.g., detect, decrypt and/or decode) data received from the user via an input device 156 that may include one or more buttons or other input elements, which may be physical or graphical (e.g., a touch-sensitive screen) and embedded into the housing 115 of the electronic cigarette 100. As another example, in some embodiments, the user interface 150 may include suitable circuitry and/or software for controllably illuminating a tip of the electronic cigarette 100 as specified by the controller 160 (such as when vaping is in progress). As yet another example, in some embodiments, the user interface 150 may be configured for outputting of information, including possible textual and/or graphical and/or video data, via a screen or other visual output device. As yet another example, in some embodiments, the user interface 150 may include a biometric sensor to sense a biometric feature of the user (e.g., a fingerprint sensor) in order to identify and/or authenticate the user.

The controller 160 comprises suitable circuitry and/or software for sending signals to and receiving signals from other components of the electronic cigarette 100 to which it is connected, including, in this embodiment, the user interface 150, the power source 110, and the vapor producer 120, in order to control operation of the electronic cigarette 100.

In some embodiments, the control system 130 may also include a communication interface 170 that may be connected to the controller 160 and may include suitable circuitry and/or software for interacting with one or more external communication devices over one or more communication links. Thus, certain inputs received by the controller 160, rather than being received via the user interface 150, can be received via the communication interface 170.

Figure 7:
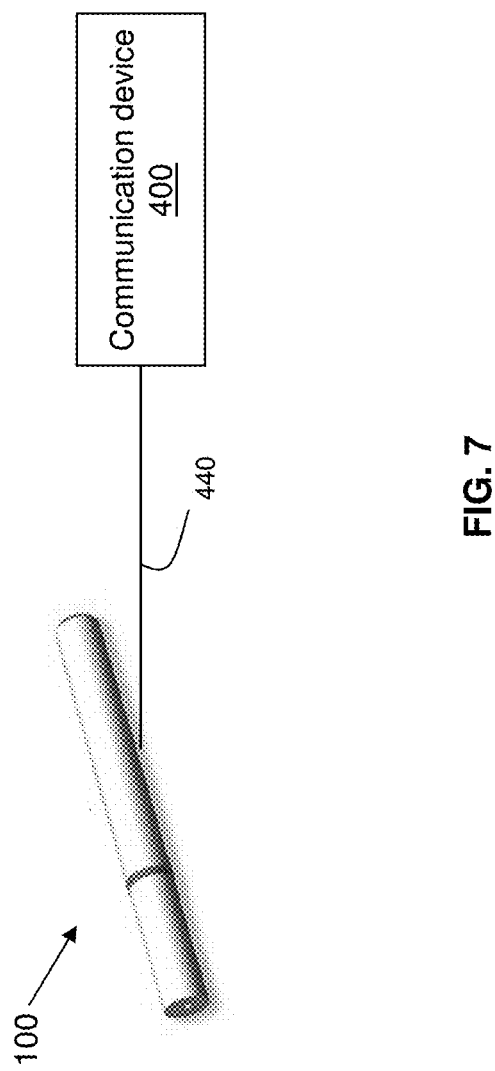
FIG. 7 shows an example of a communication device connected to the electronic vaping device.

For instance, with additional reference to FIG. 7, a communication device 400 that is external to the electronic cigarette 100 may interact with the electronic cigarette 100 over a communication link 440, which may be wireless, wired, or partly wireless and partly wired (e.g., Bluetooth or other short-range or near-field wireless connection, WiFi or other wireless LAN, WiMAX or other wireless WAN, cellular, Universal Serial Bus (USB), etc.). For example, in some embodiments, the communication device 400 may be:

- a smartphone or other wireless phone; a tablet computer; a head-mounted display, smartwatch or other wearable device; or any other communication device carried, worn or otherwise associated with the user of the electronic cigarette 100 or another individual proximate to the electronic cigarette 100;
- a server or other computing apparatus (e.g., implementing a website) associated with: a manufacturer of the electronic cigarette 100; a government authority; a retailer/distributor/vendor of the electronic cigarette 100; a physician or other medical professional authorized to regulate vaping on behalf of the user; a pharmacist or other dispensing entity authorized to regulate vaping on behalf of the user; a telecommunications provider (telco) or Internet Service Provider (ISP) authorized to communicate with the electronic cigarette 100; or any other party who may have an interest in the electronic cigarette 100 and/or its use;
- another electronic cigarette with communication capabilities;
- etc.

In some cases, such as where the communication device 400 is a smartphone, tablet, head-mounted display, smartwatch, or other communication device carried or worn by the user of the electronic cigarette 100, or even another electronic cigarette, communication between the electronic cigarette 100 and the communication device 400 may be direct, i.e., without any intermediate device. For instance, in some embodiments, this can be achieved by pairing (e.g., Bluetooth pairing) the electronic cigarette 100 with the communication device 400.

In other cases, such as where the communication device 400 is a server remote from the electronic cigarette 100, communication between the electronic cigarette 100 and the communication device 400 may be indirect, e.g., through one or more networks and/or one or more additional communication devices. For example, in some embodiments, the electronic cigarette 100 may communicate with a WiFi hotspot or cellular base station, which may provide access to a service provider and ultimately the Internet or another network, thereby allowing the electronic cigarette 100 and the communication device 400 to communicate (e.g., exchange information). As another example, in some embodiments, communication between the electronic cigarette 100 and the communication device 400 may take place through a smartphone, tablet, head-mounted display, smartwatch, or other communication device which is carried or worn by the user of the electronic cigarette 100 and which itself may have established communication with a WiFi hotspot or cellular base station.

The electronic cigarette 100, including certain components mentioned herein, may be implemented in various ways. For example, in some embodiments, certain components of the electronic cigarette 100 may be implemented as in a commercially available electronic cigarette such as V2cigs™ electronic cigarettes, which are described, for instance, on web pages available at http://www.v2cigs.com/ and incorporated by reference herein, or as Blu™ electronic cigarettes, which are described, for instance, on web pages available at http://www.blucigs.com/blu-starter-pack and hereby incorporated by reference herein, or as Smokio™ electronic cigarettes, which are described, for instance, on web pages available at http://www.smokio.com and hereby incorporated by reference herein. As another example, in some embodiments, certain components of the electronic cigarette 100 may be implemented as described in U.S. Patent Application Publication 2011/0265806, which is incorporated by reference herein.

I. Altering of Vapor-Providing Capability

In some embodiments, the controller 160 is configured to cause a vapor-providing capability of the electronic cigarette 100, i.e., a capability of the electronic cigarette 100 to provide vapor through the outlet 152, to be altered in response to one or more events.

An event in response to which the controller 160 causes the vapor-providing capability of the electronic cigarette 100 to be altered, which will be referred to as a "local vapor-providing capability alteration (VCA) event", may include one or more conditions being met (e.g., one or more circumstances having arisen) at the electronic cigarette 100. Any or all of these one or more conditions may be predefined or otherwise specified such that, when the one or more conditions are met, the event is deemed to have occurred.

Detection that the one or more conditions are met at the electronic cigarette 100, and therefore detection of a local VCA event, may be carried out by the controller 160. This may be achieved based on processing of one or more inputs that may be received by the controller 160. Examples of such inputs may include external inputs received via the user interface 150 and/or the communication interface 170 and/or internal inputs from various internal components (e.g., a clock, a GPS locator, a battery, etc.) of the electronic cigarette 100.

When a local VCA event is detected, the controller 160 responds by effecting a control action to alter the vapor-providing capability of the electronic cigarette 100.

For example, in some embodiments, the controller 160 may be configured to cause the vapor-providing capability of the electronic cigarette 100 to be disabled in response to a local VCA event other than (i.e., different from) a manual shutdown of the electronic cigarette 100. The manual shutdown of the electronic cigarette 100 is a process by which an individual touches the electronic cigarette 100 in order to shut down the electronic cigarette 100. This involves touching the user interface 150 (e.g., a power button or one or more other control elements of the user interface 150) at a predefined location or in accordance with a predefined technique that will cause the electronic cigarette 100 to shut down, or removing the battery 112 from the electronic cigarette 100 to shut down the electronic cigarette 100.

For instance, in various embodiments, the controller 160 may be configured to cause the vapor-providing capability of the electronic cigarette 100 to be disabled in response to an external control signal from the communication device 400 that is external to the electronic cigarette 100 (e.g., a "remote" disablement), or in response to one or more conditions independent of user input, such as a time- and/or location-dependent condition, having arisen (e.g., an "automatic" disablement), as will be further discussed later.

Accordingly, when its vapor-providing capability is disabled by the controller 160, the electronic cigarette 100 will not provide vapor drawable through the outlet 152, even during a person's attempt to draw (e.g., puff, inhale, etc.) vapor through the outlet 152 while the electronic cigarette 100 is powered on.

Causing the vapor-providing capability of the electronic cigarette 100 to be disabled (even during an attempt to draw (e.g., puff, inhale, etc.) vapor through the outlet 152 while the electronic cigarette 100 is turned on) may be useful, for example:

- to prevent or limit vaping by an individual (i.e., the user or another person) who may not be authorized to vape the electronic cigarette 100 or who may be subject to certain vaping limitations. For instance, this may be useful to prevent a child, teenager or other under-aged individual (e.g., who may not be legally allowed to purchase or consume conventional tobacco products or electronic cigarettes) from vaping the electronic cigarette 100;
- to prevent or limit vaping of the electronic cigarette 100 by individuals in certain locations, at certain times, abiding to a smoking cessation program, afflicted by a known medical condition, and/or exhibiting an abnormal vaping pattern;
- to notify the user of a status of the vapor producer 120 (e.g., almost empty, lacks nicotine, etc.); and/or
- to notify the user of a context-dependent occurrence, which is an occurrence whose meaning would be implicitly understood by virtue of the user noticing that the vapor-providing capability of the electronic cigarette 100 has been disabled.

Figure 10:
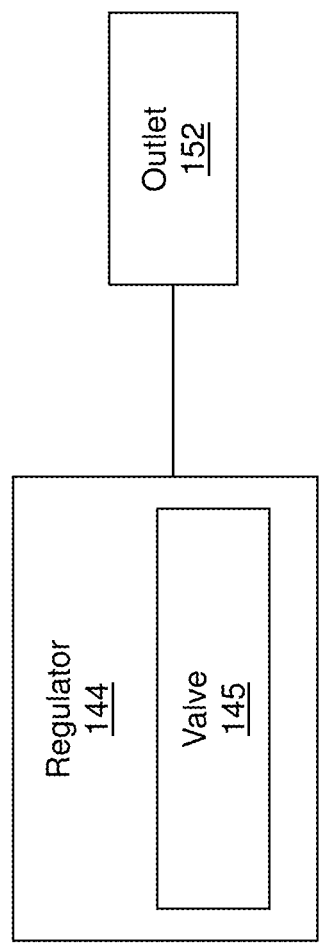

The control action that can be effected by the controller 160 in order to disable the vapor-providing capability of the electronic cigarette 100 in response to a local VCA event may be implemented in several ways in various embodiments. For instance, the control action effected by the controller 160 in response to a local VCA event can be a signaling action, such as transmission or non-transmission of an internal control signal to another component of the electronic cigarette 160. For example, in some embodiments, the control action effected by the controller 160 in response to a local VCA event may include:

- Disabling the fluid-drawing detector 154. This would prevent the issuance of a signal that would otherwise indicate that the user has drawn (e.g., puffed, inhaled, etc.) through the outlet 152. For instance, in some embodiments, as shown in FIG. 8, this may be accomplished by way of a regulator 140 including an electronic circuit device 142 which cuts off power to (i.e., disables) the fluid-drawing detector 154 when desired. Thus, instead of being connected directly to the power source 110, the fluid-drawing detector 154 is connected through the regulator 140. In some embodiments, the electrical circuit device 142 may be an electrical switch, relay, fuse, circuit breaker, etc. for altering supply of power from the power source 110 to one or more components of the fluid-drawing detector 154. Other electrical, mechanical, electromechanical, piezoelectric, magnetic, electromagnetic or other suitable devices can be used to disable the fluid-drawing detector 154;
- Ignoring the signal received from the fluid-drawing detector 154. Equivalently, this amounts to refraining from sending a vaporize enable signal to the vapor producer 120 during the relevant circumstances, even if the controller 160 were to detect from the fluid-drawing detector 154 that the user has drawn (e.g., puffed, inhaled, etc.) through the outlet 152;
- Cutting off power to one or more elements of the vapor producer 120. This would inhibit operation of the vapor producer 120 (and prevent production of vapor), even if during this time the controller 160 detects from the fluid-drawing detector 154 that the user has drawn (e.g., puffed, inhaled, etc.) through the outlet 152 and sends or attempts to send the vaporize enable signal to the vapor producer 120. In this way, even if a vaporize enable signal is sent to the vapor producer 120, no vapor will be produced. For instance, as shown in FIG. 9, in some embodiments, instead of being connected directly to the power source 110, the vapor producer 120 is connected through a regulator 141 including an electrical circuit device 143 which cuts off power to one or more components (e.g., a heater) of the vapor producer 120. Other electrical, mechanical, electromechanical, piezoelectric, magnetic, electromagnetic or other suitable devices can be used to disable the vapor producer 120;
- Preventing flow of vapor out through the outlet 152. This would prevent vapor produced by the vapor producer 120 from flowing out via the outlet 152 to the user, even if during this time the controller 160 detects from the fluid-drawing detector 154 that the user has drawn (e.g., puffed, inhaled, etc.) through the outlet 152 and sends the vaporize enable signal to the vapor producer 120. For instance, in some embodiments, as shown in FIG. 10, a regulator 144 may include a valve 145 (e.g., an electrically-controlled valve) to prevent fluid flow within the electronic cigarette 100, such as flow of the substance from the container 124 and/or flow of vapor produced by the vapor producer 120 out via the outlet 152; and/or
- etc.

While in examples considered above an alteration of the vapor-providing capability of the electronic cigarette 100 in response to a local VCA event is a disablement of this vapor-providing capability, in other embodiments, the controller 160 may be configured to cause the vapor-providing capability of the electronic cigarette 100 to be altered in other ways (e.g., reduced, enabled or increased) in response to a local VCA event.

In some embodiments, the controller 160 implements an algorithm (e.g., a program) to effect a control action to alter the vapor-producing capability of the electronic cigarette 100 in response to a local VCA event. The algorithm can be encoded in a set of computer-readable instructions executed by the controller 160 (e.g., by a processor of the controller 160). The computer-readable instructions may be stored in a memory embedded in the controller 160 or located externally thereto. The algorithm takes into account one or more stimuli, which can include external inputs received via the user interface 150, external inputs received via the communication interface 170, and/or internal inputs from various internal components such as a clock, a GPS locator, a battery, etc.

Figure 11:
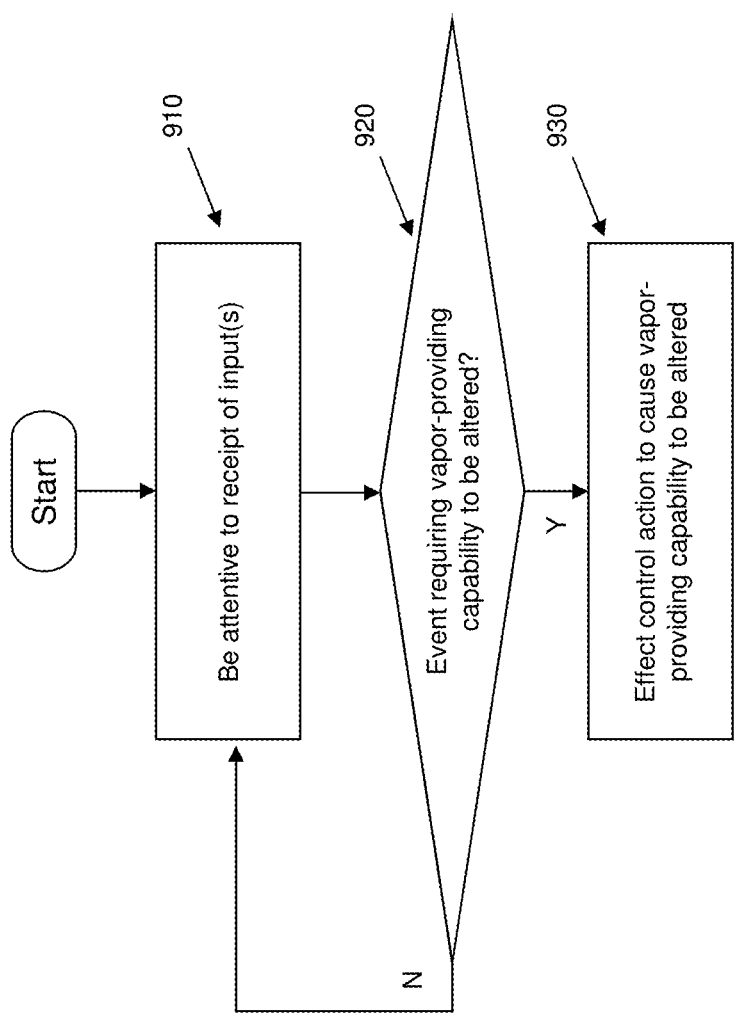
FIG. 11 shows an example of a process for altering the vapor-providing capability of the electronic vaping device.

For example, in some embodiments, the controller 160 implements an algorithm now described with additional reference to FIG. 11. Specifically, at step 910, the controller 160 is attentive to receipt of one or more inputs (e.g., external inputs received via the user interface 150, external inputs received via the communication interface 170, and/or internal inputs from various internal components such as a clock, a GPS locator, a battery, etc.). At step 920, the controller 160 determines, based on one or more inputs that may (or may no longer) be received, whether one or more conditions (e.g., circumstances) indicative of a local VCA event have arisen. In the negative, the controller 160 returns to step 910. If it determines that one or more conditions (e.g., circumstances) indicative of a local VCA event have arisen (e.g., one or more particular inputs or combinations of inputs have been received), the controller 160 proceeds to step 930, in which case the controller 160 effects the control action.

It should be appreciated that more than one set of one or more conditions (e.g., circumstances) may be indicative of a local VCA event having arisen, each causing the controller 160 to execute step 930 and effect the control action.

In some cases, a local VCA event involves receipt of an explicit command to alter the vapor-providing capability of the electronic cigarette 100. Specifically, as part of step 920, the controller 160 may verify whether an external input received at step 910 via the user interface 150 and/or the communication interface 170 is an "external VCA command". As such, at step 920, the controller 160 processes and interprets the external inputs received via the user interface 150 and/or the communication interface 170 and, if it is found that an external VCA command has been received and that the receipt of the external VCA command (possibly along with one or more other circumstances having arisen at the electronic cigarette 100) is such that a local VCA event is deemed to have occurred, proceeds to step 930 to effect the control action.

The external VCA command may in some cases be received via the user interface 150 and in other cases via the communication interface 170. In the case where the external VCA command is received via the user interface 150, this may occur by the user manipulating a screen or via certain dedicated buttons (e.g., other than a power switch). As such, the user's desire to alter the vapor-providing capability of the electronic cigarette 100 is effectively translated into a VCA command.

In the case where the external VCA command is received via the communication interface 170, the external VCA command may in some cases originate from the communication device 400, which issues the VCA command in response to detection of a "remote VCA event". The remote VCA event may include one or more conditions being met (e.g., one or more circumstances having arisen) outside the electronic cigarette 100, namely at the communication device 400.

Detection that the one or more conditions are met at the communication device 400, and therefore detection of a remote VCA event, may be carried out by processing circuitry at the communication device 400 running a program. The program may include a set of computer-readable instructions stored in a memory embedded in the communication device 400 or located externally thereto. The program takes into account one or more stimuli. Examples of such stimuli may include external inputs received via a user interface and/or a communication interface of the communication device 400 and/or internal inputs from various internal components (e.g., a clock, a GPS locator, a battery, etc.) of the communication device 400.

Thus, when the communication device 400 detects a remote VCA event, the communication device 400 responds by sending an external VCA command to the electronic cigarette 100. Upon receipt at the electronic cigarette 100, the external VCA command is interpreted by the controller 160 and, assuming that the receipt of the external VCA command (possibly along with one or more other circumstances having arisen at the electronic cigarette 100) is such that a local VCA event is deemed to have occurred, the controller 160 effects a control action to alter the vapor-providing capability of the electronic cigarette 100.

Various techniques exist for providing the external VCA command via the user interface 150 and/or the communication interface 170 including, for example, those discussed below.

1—Direct

In the direct technique, the input device 156 of the user interface 150 of the electronic cigarette 100 (e.g., including one or more buttons, a touch screen and/or any other input mechanism) allows the user to directly enter the external VCA command into the electronic cigarette 100. The input device 156 may in some cases allow the user to indicate: whether vaping is to be enabled; whether vaping is to be disabled, a degree of vaping to be permitted; and/or an increase or decrease in allowable vaping intensity. Additionally or alternatively, in some cases, the user may use the input device 156 in respect of a particular constituent (e.g., nicotine, AWOL) that may be contained in the vapor, such as to indicate: whether the particular constituent is to be contained or not contained in the vapor; a degree of the particular constituent to be contained in the vapor; and/or an increase or decrease in an amount of the particular constituent. Where multiple flavors are provided, and where the electronic cigarette 100 includes a mechanism for individually dispensing these flavors, flavorings may similarly be combined in different ratios on a customized basis.

2—Paired

In the paired technique, a specific communication device (or a group of specific communication devices) is paired with the electronic cigarette 100, such that only signals received from the specific communication device (or the group of specific communication devices) are recognized as valid. The specific communication device can be a smartphone or other mobile phone, a tablet, a smart watch, head-mounted display or other wearable device, etc., or even another electronic cigarette.

For example, in some embodiments, the user may download an application (app) from a repository (e.g., Apple's App Store, iTunes, Google Play, Android Market, etc.) onto the specific communication device that is paired with the electronic cigarette 100. Upon activation of the app on the specific communication device, the user may access certain features to control certain aspects of the electronic cigarette 100 (including the vapor-providing capability of the electronic cigarette 100) locally on the specific communication device. This can be achieved by sending an external VCA command from the specific communication device to the electronic cigarette 100. In addition, a data connection can be established over the Internet with a server of which executes a complementary server-side application interacting with the app on the specific communication device.

3—Addressed

In the addressed technique, the electronic cigarette 100 is assigned a network identifier, such as an IP address, and is able to communicate over a network with other devices having IP addresses. As such, knowledge of the electronic cigarette's IP address allows other networked devices to communicate with the electronic cigarette 100. Such communication may include transmission of the external VCA command to the electronic cigarette 100.

4—Out-of-Band

In the out-of-band technique, a communication channel is reserved for emergency or administrative use rather than data communication with other networked devices. For example, this could include a reserved frequency (in the case of an FDMA system), a reserved multiplexing code (in the case of a CDMA system), a reserved time slot (in the case of a TDMA system), a reserved encryption key (in the case of a digital system) or a reserved network identifier (e.g., IP address). This can allow operational control of the electronic cigarette 100 to be overridden and controlled by an external entity, such as in an emergency or where mandated by law. Thus, the external VCA command could be sent over the reserved communication channel.

In case 1 identified above, the external VCA command is provided by the user at an instant chosen by the user.

In each of cases 2, 3 and 4 identified above, the external VCA command is issued by a communication device that is external to the electronic cigarette 100 and conveyed via a communication link, which may be wireless, wired, or partly wireless and partly wired (e.g., Bluetooth, WiFi or other wireless LAN, WiMAX or other wireless WAN, cellular, USB, etc.), such as the communication device 400 and the communication link 440 discussed above in connection with FIG. 7. For example: in the paired technique, the communication device 400 may be a smartphone or other mobile phone, a tablet, a smart watch, head-mounted display or other wearable device, or any other communication device that may be carried by the user, and the communication link 440 may a short-range wireless link (e.g., Bluetooth) or a wired link (e.g., USB); in the addressed technique, the communication device 400 may be a server or other computing apparatus or a smartphone or other mobile phone, a tablet, a smart watch, head-mounted display or other wearable device, or any other communication device that may be carried by the user and the communication link 440 may be implemented by a data network such as the Internet over a wired connection and/or a wireless connection (e.g., WiFi, WiMAX, cellular, etc.); and, in the out-of-band technique, the communication device 400 may be a server or other computing apparatus and the communication link 440 may be implemented over a wireless connection using, for instance, dedicated short-range communication (DSRC), IEEE 802.11, Bluetooth and CALM (Communications Access for Land Mobiles), RFID, etc.

VCA events (whether local or remote) may be defined by one or more conditions (e.g., circumstances) that may involve various factors, including, for example, one or more of:
  an indication of a desire of the user to alter (e.g., enable, disable, increase or decrease) the vapor-providing capability of the electronic cigarette 100;
  an identity of the user (e.g., to prevent any other individual or any person not authorized to vape to use the electronic cigarette 100);
  a location of the electronic cigarette 100 (e.g., to prevent or limit vaping in restaurants, movie theatres, hospitals and other medical establishments, and other public places; airplanes, trains, cars and other vehicles; etc.; and/or to prevent or limit vaping when the electronic cigarette 100 is deemed to be located not in proximity to the user);
  time (e.g., to prevent or limit vaping at certain times of day or other specified moments; and/or to prevent vaping after a predetermined period has lapsed since the electronic cigarette 100 was last used to vape);
  a smoking cessation program of the user (e.g., to prevent the user from vaping more frequently, longer, etc. than permitted under the smoking cessation program);
  a medical condition of the user (e.g., to prevent or limit vaping that could detrimentally affect the user's heath);
  a manner in which the user draws on the outlet 152 of the electronic cigarette 100, such as an abnormal vaping pattern (e.g., vape inhalation duration or frequency);
  a status of the container 124 of the vapor producer 120, such as fill level (e.g., full, empty, remaining quantity, etc.) of the container 124 (e.g., if almost empty, a first vape in a new series of vapes can be restricted to remind the user that he/she soon will need to change or replenish the container 124);
  a refilling of a depletable resource of the electronic cigarette 100 (e.g., a recharging of the battery 112, a replacement of the container 124 of the vapor producer 120, or a replenishing of the substance contained in the container 124); and/or
  a result or progression of game play on a game station in a vicinity of the electronic cigarette 100 (e.g., to allow, enable or facilitate vaping in an arcade or a casino in response to game play, thereby to encourage customers to stay and continue to play in the arcade or casino); etc.

Examples of embodiments in which the controller 160 can cause the vapor-providing capability of the electronic cigarette 100 to be disabled or otherwise altered in response to a local VCA event will now be discussed. In particular, most of these examples will focus on detection of remote VCA events by the communication device 400, followed by issuance of an external VCA command, followed by detection of a local VCA event (i.e., receipt of the external VCA command, possibly along with one or more other circumstances having arisen at the electronic cigarette 100), followed by altering of the vapor-providing capability of the electronic cigarette 100. However, it should be understood that a similar description could be provided if, instead of detecting remote VCA events at the communication device 400, one were to describe detecting equivalent local VCA events at the controller 160.

Example 1

In some embodiments, as shown in FIG. 12, the communication device 400 is a mobile communication device (e.g., a smartphone or other wireless phone; a tablet computer; a head-mounted display, smartwatch or other wearable device; etc.) of the user which runs a software application (e.g., a mobile app) that relates to the electronic cigarette 100 and monitors user input through the user interface of the mobile communication device 400. The user input may indicate a desire of the user to alter (e.g., enable, increase, disable, or decrease) the vapor-providing capability of the electronic cigarette 100. The software application translates the user input into an external VCA command and transmits the external VCA command to the electronic cigarette 100 over the communication link 440, which is a wireless connection.

Upon receipt of the external VCA command by the communication interface 170 of the electronic cigarette 100, the controller 160 processes the external VCA command and effects a control action in order to alter the vapor-providing capability of the electronic cigarette 100 in accordance with the user's desire. For instance, the controller 160 may send or refrain from sending an internal control signal to the vapor producer 120, the fluid-drawing detector 154, etc., to disable or otherwise alter the vapor-providing capability of the electronic cigarette 100 in accordance with the user's desire.

For instance, in various examples of situations, this may be useful for the user to: enable the vapor-providing capability of the electronic cigarette 100 when he/she wants to vape; disable the vapor-providing capability of the electronic cigarette 100 when he/she does not want to or cannot vape; disable the vapor-providing capability of the electronic cigarette 100 when he/she wants no one else to use the electronic cigarette 100 (e.g., if the electronic cigarette 100 is not with him/her, is near a child, etc.); decrease or increase an amount of a constituent (e.g., nicotine) of the vapor that can be vaped; etc.

Example 2

In some embodiments, as shown in FIG. 13, the communication device 400 is a mobile communication device (e.g., a smartphone or other wireless phone; a tablet computer; a head-mounted display, smartwatch or other wearable device; etc.) of the user which runs a software application that relates to the electronic cigarette 100 and monitors a time of day to disable the vapor-providing capability of the electronic cigarette 100 during one or more predetermined periods (e.g., during normal work hours or sleep hours of the user). When the software application determines that a predetermined period during which the vapor-providing capability of the electronic cigarette 100 is to be disabled has arrived, it transmits an external VCA command to the electronic cigarette 100 over the communication link 440, which is a wireless connection.

Upon receipt of the external VCA command by the communication interface 170 of the electronic cigarette 100, the controller 160 processes the external VCA command and effects a control action in order to disable the vapor-providing capability of the electronic cigarette 100. For instance, the controller 160 may send or refrain from sending an internal control signal to the vapor producer 120, the fluid-drawing detector 154, etc., to disable the vapor-providing capability of the electronic cigarette 100.

Conversely, when the software application determines that the predetermined period during which the vapor-providing capability of the electronic cigarette 100 is to be disabled is over, it transmits another external VCA command to the electronic cigarette 100 over the wireless connection 440. In response to this external VCA command, the controller 160 effects a control action in order to enable the vapor-providing capability of the electronic cigarette 100. For instance, the controller 160 may send an internal control signal to the vapor producer 120, the fluid-drawing detector 154, etc., to enable the vapor-providing capability of the electronic cigarette 100.

In a variant, in some embodiments, the software application running on the mobile communication device 400 may send an external VCA command to the electronic cigarette 100 to enable the vapor-providing capability of the electronic cigarette 100 when it determines that a predetermined period during which the vapor-providing capability of the electronic cigarette 100 is to be enabled has arrived.

For instance, in various examples of situations, this may be useful to prevent vaping of the electronic cigarette 100 by the user during periods that the user cannot or should not vape, prevent vaping of the electronic cigarette 100 by an individual (e.g., a child) not authorized to vape the electronic cigarette 100 during periods of time when the user is unlikely to be in a position to be able to prevent such unauthorized vaping; etc.

Example 3

In some embodiments, as shown in FIG. 14, the communication device 400 is a mobile communication device (e.g., a smartphone or other wireless phone; a tablet computer; a head-mounted display, smartwatch or other wearable device; etc.) of the user which runs a software application that relates to the electronic cigarette 100 and that monitors a proximity of the mobile communication device 400 to the electronic cigarette 100 in order to disable the vapor-providing capability of the electronic cigarette 100 when the electronic cigarette 100 is deemed to no longer be proximate enough to the mobile communication device 400, which is presumed to be with the user. It should be appreciated that proximity may be assessed in various ways, such as by comparing the actual location of the mobile communication device 400 to that of the electronic cigarette 100, or by detecting a distance (e.g., based on signal strength, signal travel time, etc.) between the mobile communication device 400 and the electronic cigarette 100, to name a few possibilities. Thus, when the software application determines that the mobile communication device 400 and the electronic cigarette 100 are not within a specified distance (e.g., 1 or 2 m) from one another, the mobile communication device 400 sends an external VCA command to the electronic cigarette 100 over the communication link 440, which is a wireless connection, in order to disable vaping.

Upon receipt of the external VCA command by the communication interface 170 of the electronic cigarette 100, the controller 160 processes the external VCA command and effects a control action in order to disable the vapor-providing capability of the electronic cigarette 100. For instance, the controller 160 may send or refrain from sending an internal control signal to the vapor producer 120, the fluid-drawing detector 154, etc., to disable the vapor-providing capability of the electronic cigarette 100.

In a variant, in some embodiments, the software application running on the mobile communication device 400 may send an external VCA command to the electronic cigarette 100 to enable the vapor-providing capability of the electronic cigarette 100 when it determines that the mobile communication device 400 and the electronic cigarette 100 are within a specified distance from one another.

For instance, in various examples of situations, this may be useful to prevent vaping of the electronic cigarette 100 by any individual when the electronic cigarette 100 is presumably not near the user (assuming that the mobile communication device 400 is carried by the user), which may deter unauthorized use (e.g., by a child) or theft of the electronic cigarette 100. In other situations, if the user experiences a sudden inability to draw vapor, this may alert the user to the potential that he/she has misplaced the mobile communication device 400 or that it has been stolen.

Example 4

In some embodiments, as shown in FIG. 15, the communication device 400 is a mobile communication device (e.g., a smartphone or other wireless phone; a tablet computer; a head-mounted display, smartwatch or other wearable device; etc.) of the user which runs a software application that monitors usage of the electronic cigarette 100 (e.g., a vaping pattern) and disables the vapor-providing capability of the electronic cigarette 100 when a certain amount of time (e.g., 2 minutes) has elapsed since the last vape. To that end, the controller 160 of the electronic cigarette 100 may monitor vaping activity (e.g., maintain a vaping log noting times at which vapes occur based on inputs from the fluid-drawing detector 154) and the communication interface 170 may repeatedly (e.g., periodically) transmit a signal indicative of the vaping activity to the mobile communication device 400 over the communication link 440, which is a wireless connection. Based on the received signal indicative of the vaping activity, when the software application running on the mobile communication device 400 determines that a certain amount of time has elapsed since the last vape, the mobile communication device 400 sends an external VCA command to the electronic cigarette 100 over the wireless connection 440 in order to disable vaping.

Upon receipt of the external VCA command by the communication interface 170 of the electronic cigarette 100, the controller 160 processes the external VCA command and effects a control action in order to disable the vapor-providing capability of the electronic cigarette 100. For instance, the controller 160 may send or refrain from sending an internal control signal to the vapor producer 120, the fluid-drawing detector 154, etc., to disable the vapor-providing capability of the electronic cigarette 100.

When the user desires to once again vape the electronic cigarette 100, he/she may interact with the user interface of the mobile communication device 400 in order to provide user input to enable the vapor-providing capability of the electronic cigarette 100. For instance, in some embodiments, the software application running on the mobile communication device may provide an option (e.g., via a button or other control element) selectable by the user to enable the vapor-providing capability of the electronic cigarette 100. In some cases, the user may be required to input credentials (e.g., a password) to authenticate himself/herself. In response to receiving user input indicative of the user's desire to enable the vapor-providing capability of the electronic cigarette 100, the mobile communication device 400 sends an external VCA command to the electronic cigarette 100 over the wireless connection 440 in order to enable vaping.

Upon receipt of the external VCA command by the communication interface 170 of the electronic cigarette 100, the controller 160 processes the external VCA command and effects a control action in order to enable the vapor-providing capability of the electronic cigarette 100. For instance, the controller 160 may send an internal control signal to the vapor producer 120, the fluid-drawing detector 154, etc., to enable the vapor-providing capability of the electronic cigarette 100.

For instance, in various examples of situations, this may be useful to prevent vaping of the electronic cigarette 100 by any individual when the electronic cigarette 100 has not been vaped by the user for some time, which may deter unauthorized use (e.g., by a child) or theft of the electronic cigarette 100.

Example 5

Figure 16:
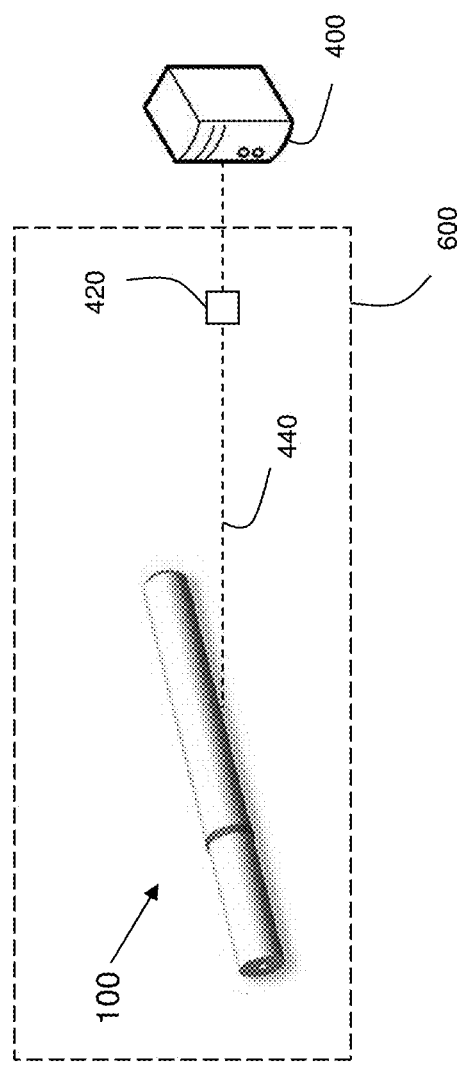

In some embodiments, as shown in FIG. 16, the communication device 400 is a server associated with a vaping-prohibited area 600 of a particular site, such as an airport, airplane, hospital, restaurant, school, movie theater, train, subway, bus, rental car, or other public place or vehicle, etc. and issues an external VCA command to disable the vapor-providing capability of any electronic cigarette in range of a wireless transmitter 420 located in or near the vaping-prohibited area 600 and implementing part of the communication link 440, which includes a wireless connection. To that end, controllers of electronic cigarettes such as the controller 160 of the electronic cigarette 100 are configured to recognize the external VCA command as a command to disable vaping of the electronic cigarette. The external VCA command may be repeatedly or continually issued so as to ensure that electronic cigarettes that newly enter the vicinity of the vaping-prohibited area 600 will receive the external VCA command. In some cases, the server 400 may be located at the vaping-prohibited area 600, along with the wireless transmitter 420 (e.g., which may be part of the server 400 or physically separate from and connected to the server 400). In other cases, the server 400 may be located remotely from the vaping-prohibited area 600 and connected to the wireless transmitter 420 over the communication link 440.

Thus, when the electronic cigarette 100 enters the vaping-prohibited area 600 and becomes within range of the wireless transmitter 420, the external VCA command is received by the communication interface 170 of the electronic cigarette 100. The controller 160 processes the external VCA command and effects a control action in order to disable the vapor-providing capability of the electronic cigarette 100. For instance, the controller 160 may send or refrain from sending an internal control signal to the vapor producer 120, the fluid-drawing detector 154, etc., to disable the vapor-providing capability of the electronic cigarette 100. As long as the electronic cigarette 100 continues to receive the external VCA command from the wireless transmitter 420, the controller 160 maintains the vapor-providing capability of the electronic cigarette 100 disabled.

Conversely, when the electronic cigarette 100 subsequently leaves the vaping-prohibited area 600 and becomes out of range of the wireless transmitter 420, the external VCA command ceases to be received by the communication interface 170 of the electronic cigarette 100. The controller 160 detects this absence of receipt of the external VCA command (e.g., the external VCA command has not been received for a predetermined period of time, such as 30 seconds for instance) and effects a control action in order to enable the vapor-providing capability of the electronic cigarette 100. For instance, the controller 160 may send an internal control signal to the vapor producer 120, the fluid-drawing detector 154, etc., to enable the vapor-providing capability of the electronic cigarette 100.

For instance, in various examples of situations, this may be useful to prevent vaping of any electronic cigarette such as the electronic cigarette 100 where vaping is not permitted. In various other examples of situations, this may be useful to prevent vaping of any electronic cigarette such as the electronic cigarette 100 where vaping is undesirable (e.g., to avoid inconveniencing or adversely affecting other individuals who are or could subsequently be located there).

Example 6

Figure 17:
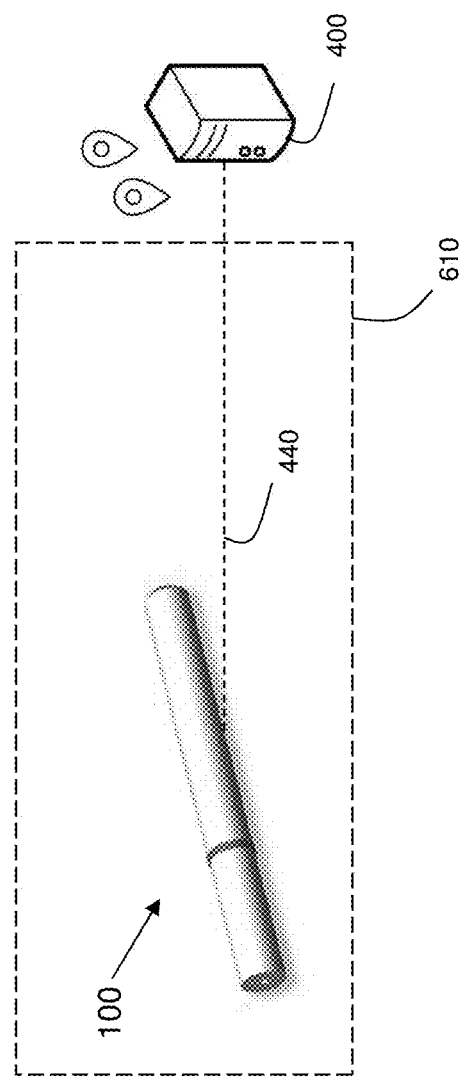

In some embodiments, as shown in FIG. 17, the communication device 400 is a server which runs a software application that monitors locations of electronic cigarettes and issues an external VCA command to disable the vapor-providing capability of any electronic cigarette found within a certain distance of a vaping-prohibited area 610 whose location is known, such as a recorded landmark (e.g., an airport, hospital, restaurant, school, etc.), a vehicle whose location is tracked (e.g., an airplane, public transit vehicle, rental car, etc.), etc., via the communication link 440, which includes a wireless connection. In some examples, the electronic cigarettes may be equipped with an addressing scheme (e.g., an IP address) to allow them to respond to commands directed specifically to them.

The location of the electronic cigarette 100 may be determined by the server 400 in any suitable way.

Figure 18:
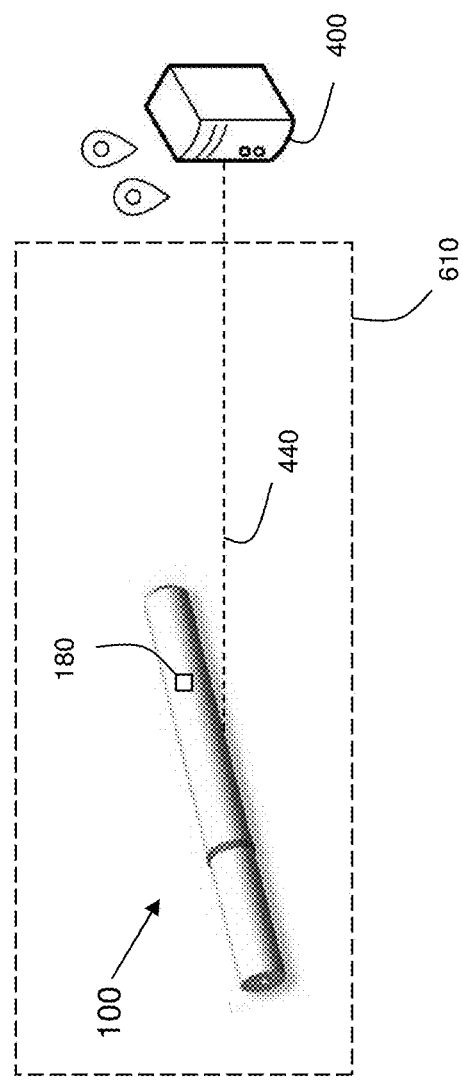

For example, in some embodiments, as shown in FIG. 18, the location of the electronic cigarette 100 may be derived from a signal transmitted by the electronic cigarette 100 itself. For instance, the electronic cigarette 100 may comprise a locator 180 (e.g., a GPS locator) which emits a wireless signal allowing the location of the electronic cigarette 100 to be identified.

Figure 19:
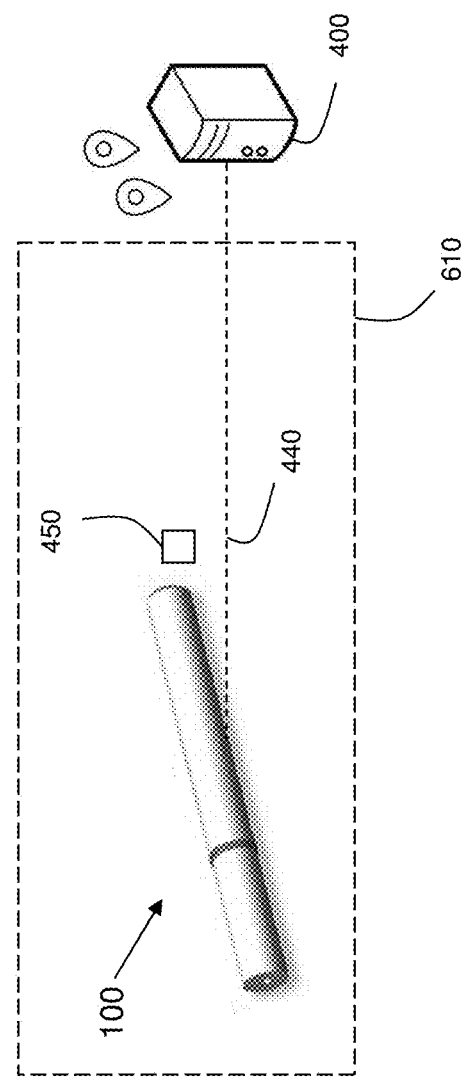
Figure 20:
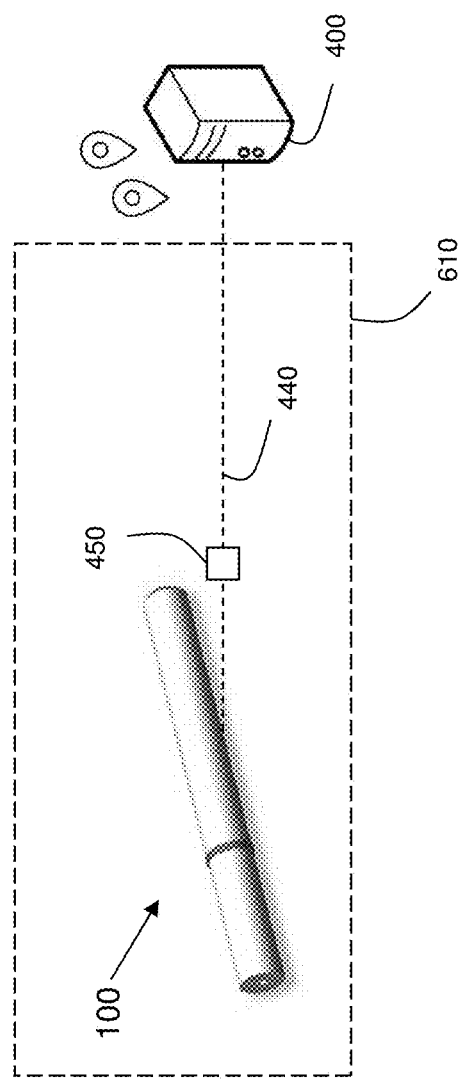

As another example, in some embodiments, as shown in FIGS. 19 and 20, the electronic cigarette 100 may be paired with a mobile communication device 450 (e.g., a smartphone or other wireless phone; a tablet computer; a head-mounted display, smartwatch or other wearable device; etc.) that is carried or worn by the user of the electronic cigarette 100 and that includes a locator (e.g., a GPS locator) which emits a wireless signal allowing a location of the mobile communication device 450 to be identified, thereby allowing the location of the electronic cigarette 100 to be inferred (assuming the electronic cigarette 100 is in the vicinity of the mobile communication device 450). In some cases, as shown in FIG. 19, the mobile communication device 450 may be used only for locating the electronic cigarette 100, without being used to convey the external VCA command from the server 400 to the electronic cigarette 100 (i.e., the mobile communication device 450 is not part of the communication link 440). In other cases, as shown in FIG. 20, the mobile communication device 450 may be used both to locate the electronic cigarette 100 and to convey the external VCA command from the server 400 to the electronic cigarette 100 (i.e., the mobile communication device 450 is part of the communication link 440, basically acting as a relay). In these cases, the mobile communication device 450 may execute a software application to interact with the server 400 over a communication link, which may be implemented by the communication link 440 or a different communication link, and the server 400 maintains an association between the mobile communication device 450 and the electronic cigarette 100 (e.g., in a database associating identifiers (e.g., serial numbers, IP addresses, etc.) of electronic cigarettes with corresponding identifiers (e.g., serial numbers, IP addresses, phone numbers, etc.) of mobile communication devices).

The location of the vaping-prohibited area 610 may be known to the server 400 in any suitable way. For example, the server 400 may have access to a database maintaining locations of vaping-prohibited areas, which may be derived from maps, vehicle-tracking systems, etc.

Thus, when the server 400 determines, based on the location of the electronic cigarette 100 and the location of the vaping-prohibited area 610, that the electronic cigarette 100 enters the vaping-prohibited area 610, the external VCA command is transmitted by the server 400 and received by the communication interface 170 of the electronic cigarette 100. The controller 160 processes the external VCA command and effects a control action in order to disable the vapor-providing capability of the electronic cigarette 100. For instance, the controller 160 may send or refrain from sending an internal control signal to the vapor producer 120, the fluid-drawing detector 154, etc., to disable the vapor-providing capability of the electronic cigarette 100. As long as the location of the electronic cigarette 100 and the location of the vaping-prohibited area 610 indicates that the electronic cigarette 100 is located at the vaping-prohibited area 610, the controller 160 maintains the vapor-providing capability of the electronic cigarette 100 disabled.

Conversely, when the server 400 determines, based on the location of the electronic cigarette 100 and the location of the vaping-prohibited area 610, that the electronic cigarette 100 leaves the vaping-prohibited area 610, the server 400 transmits an external VCA command to the electronic cigarette 100 in order to enable the vapor-providing capability of the electronic cigarette 100. Once the external VCA command is received by the communication interface 170 of the electronic cigarette 100, the controller 160 processes this external VCA command and effects a control action in order to enable the vapor-providing capability of the electronic cigarette 100. For instance, the controller 160 may send an internal control signal to the vapor producer 120, the fluid-drawing detector 154, etc., to enable the vapor-providing capability of the electronic cigarette 100.

For instance, in various examples of situations, this may be useful to prevent vaping of any electronic cigarette such as the electronic cigarette 100 where vaping is not permitted or is undesirable (e.g., to avoid inconveniencing or adversely affecting other individuals who are or could subsequently be located there), and where the location and/or size of the vaping-prohibited area 610 can be configured.

Example 7

Figure 21:
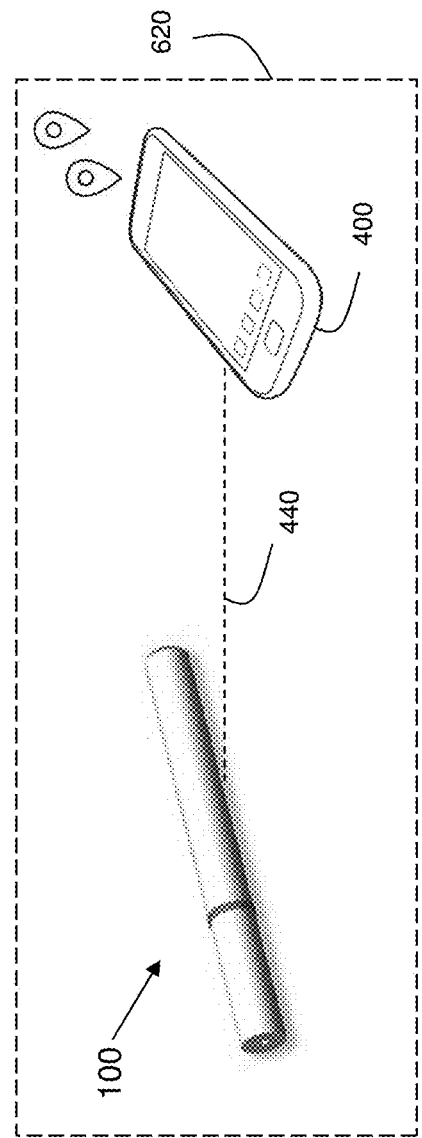

In some embodiments, as shown in FIG. 21, the communication device 400 is a mobile communication device (e.g., a smartphone or other wireless phone; a tablet computer; a head-mounted display, smartwatch or other wearable device; etc.) of the user which runs a software application that relates to the electronic cigarette 100 and that monitors a location of the mobile communication device 400, and thus a location of the electronic cigarette 100 (assuming the electronic cigarette 100 is in the vicinity of the mobile communication device 400), in order to disable the vapor-providing capability of the electronic cigarette 100 when the electronic cigarette 100 is deemed to be within a certain distance of a vaping-prohibited area 620 whose location is known, such as a recorded landmark (e.g., an airport, hospital, restaurant, school, etc.), a vehicle whose location is tracked (e.g., an airplane, public transit vehicle, rental car, etc.), etc.

The mobile communication device 400 includes a locator (e.g., a GPS locator) which emits a wireless signal allowing the location of the mobile communication device 400 to be identified, thereby allowing the location of the electronic cigarette 100 to be inferred (assuming the electronic cigarette 100 is in the vicinity of the mobile communication device 400).

The location of the vaping-prohibited area 620 may be known to the mobile communication device 400 in any suitable way. For example, the software application running on the mobile communication device 400 may have access to a database maintaining locations of vaping-prohibited areas, which may be derived from maps, vehicle-tracking systems, etc.

When the mobile communication device 400 determines, based on the location of the electronic cigarette 100 and the location of the vaping-prohibited area 620, that the electronic cigarette 100 enters the vaping-prohibited area 620, the mobile communication device 400 transmits an external VCA command to the electronic cigarette 100 over the communication link 440, which includes a wireless connection, to disable the vapor-providing capability of the electronic cigarette 100.

Upon the external VCA command being received by the communication interface 170 of the electronic cigarette 100, the controller 160 processes the external VCA command and effects a control action in order to disable the vapor-providing capability of the electronic cigarette 100. For instance, the controller 160 may send or refrain from sending an internal control signal to the vapor producer 120, the fluid-drawing detector 154, etc., to disable the vapor-providing capability of the electronic cigarette 100. As long as the location of the electronic cigarette 100 and the location of the vaping-prohibited area 620 indicates that the electronic cigarette 100 is located at the vaping-prohibited area 620, the controller 160 maintains the vapor-providing capability of the electronic cigarette 100 disabled.

Conversely, when the software application running on the mobile communication device 400 determines, based on the location of the electronic cigarette 100 and the location of the vaping-prohibited area 620, that the electronic cigarette 100 leaves the vaping-prohibited area 620, the mobile communication device 400 transmits an external VCA command to the electronic cigarette 100 in order to enable the vapor-providing capability of the electronic cigarette 100. Once the external VCA command is received by the communication interface 170 of the electronic cigarette 100, the controller 160 processes this external VCA command and effects a control action in order to enable the vapor-providing capability of the electronic cigarette 100. For instance, the controller 160 may send an internal control signal to the vapor producer 120, the fluid-drawing detector 154, etc., to enable the vapor-providing capability of the electronic cigarette 100.

For instance, in various examples of situations, this may be useful to prevent vaping of any electronic cigarette such as the electronic cigarette 100 where vaping is not permitted or undesirable (e.g., to avoid inconveniencing or adversely affecting other individuals who are or could subsequently be located there).

Example 8

Figure 22:
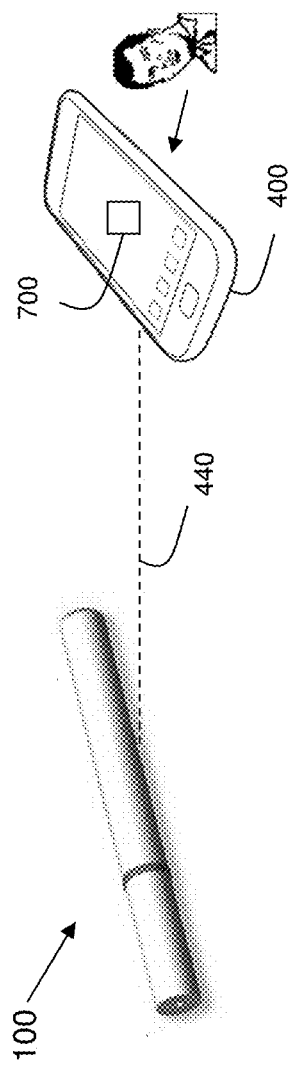

In some embodiments, as shown in FIG. 22, the communication device 400 is a mobile communication device (e.g., a smartphone or other wireless phone; a tablet computer; a head-mounted display, smartwatch or other wearable device; etc.) of the user which runs a software application that relates to the electronic cigarette 100 and that obtains authorization information 700 from the user and enables the vapor-providing capability of the electronic cigarette 100 if it determines that the authorization information 700 is valid and indicative of the user being authorized to vape. The user can interact with the user interface of the mobile communication device 400 to provide the authorization information 700 and, if the software application determines that the authorization information 700 is valid, the mobile communication device 400 issues an external VCA command to the electronic cigarette 100 over the communication link 440, which includes a wireless connection, in order to enable the vapor-providing capability of the electronic cigarette 100.

For example, in some embodiments, the authorization information 700 may comprise an identifier, such as an alphanumeric identifier (e.g., a passcode) or a biometric identifier. As another example, in other embodiments, the authorization information 700 may comprise any other information that is deemed to establish that the user is authorized to vape the electronic cigarette 100. For instance, in some cases, the authorization information 700 may include an indication of the user's age (e.g., a response to a request presented on the user interface of the mobile communication device 400 and prompting the user to indicate his/her age or confirm that he/she is at least of a certain age; an answer to a question presented on the user interface of the mobile communication device 400 to verify the user's age, etc.).

Of course, the mobile communication device 400 may provide the requisite confirmations/authentications by comparing the authentication information 700 provided by the user to previously-collected information stored in a memory. Alternatively, the mobile communication device 400 may send the authentication information 700 (or a subset thereof) to a remote server (e.g., a web server) for authentication, which may be particularly useful when a third party is to have an influence on the user's ability to vape.

Example 9

In some embodiments, as shown in FIG. 12, the communication device 400 is a mobile communication device (e.g., a smartphone or other wireless phone; a tablet computer; a head-mounted display, smartwatch or other wearable device; etc.) of the user which runs a software application (e.g., a mobile app) that relates to the electronic cigarette 100. The software application may interface with various communication utilities (including social networking/media accounts) for the user installed on the mobile communication device 400. The software application may be responsive to one or more messages (e.g., received from specific individuals and/or having specific content) to send an external VCA command to the electronic cigarette 100 over the communication link 440, which is a wireless connection. Accordingly, the external VCA command may specify whether the vapor-providing capability of the electronic cigarette 100 is to be disabled, enabled, increased (and possibly also by how much), decreased (and possibly also by how much), etc.

Upon receipt of the external VCA command by the communication interface 170 of the electronic cigarette 100, the controller 160 processes the external VCA command and effects a control action in order to alter the vapor-providing capability of the electronic cigarette 100 in accordance with what was specified in the external VCA command. As a result, the controller 160 may send or refrain from sending an internal control signal to the vapor producer 120, the fluid-drawing detector 154, etc., to disable or otherwise alter the vapor-providing capability of the electronic cigarette 100.

In some embodiments, this degree of alteration of the vapor-providing capability of the electronic cigarette 100 may be related to, for example, the originator or content of the received message(s). Thus, for example, the user may specify in the mobile app that when an email is received from John Smith, the vapor-providing capability of the electronic cigarette 100 is to be disabled. Consequently, when the user is attempting to vape the electronic cigarette 100 and is unsuccessful in drawing vapor despite seemingly normal operation of the electronic cigarette 100, the surprise absence of vapor may signal to the user the possibility that a message from John Smith may have been received.

Example 10

Figure 23:
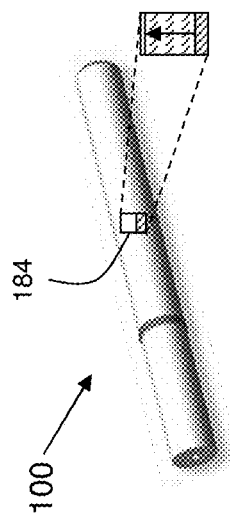

In some embodiments, as shown in FIG. 23, the vapor-providing capability of the electronic cigarette 100 may be altered (e.g., disabled) upon refilling a depletable resource 184 of the electronic cigarette 100, such as upon recharging the battery 112 or upon replacing the container 124 of the vapor producer 120 or replenishing the substance contained in the container 124. To that end, the controller 160 of the electronic cigarette 100 may monitor the depletable resource 184 of the electronic cigarette 100 and, when it determines that the depletable resource 184 is being refilled, may effect a control action to alter (e.g., disable) the vapor-providing capability of the electronic cigarette 100. The controller 160 may then, upon detecting a local VCA event (i.e., receipt of an external VCA command and/or one or more other circumstances having arisen at the electronic cigarette 100), effect another control action to once again alter (e.g., enable) the vapor-providing capability of the electronic cigarette 100. This may be useful, for instance, to reduce a potential for prolonged unauthorized use of the electronic cigarette 100 without burdening an authorized user with having to take steps (e.g., provide a password or other identifier) to establish his/her authorized use of the electronic cigarette 100 every time the electronic cigarette 100 is used.

For example, in some embodiments, as shown in FIG. 24, the depletable resource 184 of the electronic cigarette 100 may be the battery 184 such that the controller 160 of the electronic cigarette 100 monitors the battery 112 and, when it determines that the battery 112 is being recharged, effects a control action to disable the vapor-providing capability of the electronic cigarette 100. The battery 184 may be recharged using a charge source 192. For instance, in this embodiment, the charge source 192 may be implemented by a computer 194 to which the power source 110 of the electronic cigarette 100 may be connected via a cable 198 (e.g., a USB cable). The charge source 192 may be implemented in any other suitable way in other embodiments (e.g., by an electric outlet of a wall, by an inductive charging device, etc.).

When connected to the computer 194, the electronic cigarette 100 recharges the battery 184 and, upon detecting this recharging operation, the controller 160 of the electronic cigarette 100 effects a control action in order to disable the vapor-providing capability of the electronic cigarette 100. For instance, the controller 160 may send or refrain from sending an internal control signal to the vapor producer 120, the fluid-drawing detector 154, etc., to disable the vapor-providing capability of the electronic cigarette 100.

The controller 160 of the electronic cigarette 100 may then be attentive to detection of a local VCA event in order to enable the vapor-providing capability of the electronic cigarette 100. In various embodiments, the controller 100 may be attentive to receipt of one or more inputs received via the user interface 150 and/or the communication interface 170 and/or internal inputs from various internal components (e.g., a clock, a GPS locator, a battery, etc.) of the electronic cigarette 100 in order to detect a local VCA event indicating that the vapor-producing capability of the electronic cigarette 100 is to be enabled.

For instance, in some embodiments, the controller 160 of the electronic cigarette 100 may be attentive to receipt of an external VCA command from the computer 194 to which the electronic cigarette 100 is connected in order to enable the vapor-providing capability of the electronic cigarette 100.

For example, in some embodiments, while the electronic cigarette 100 is connected to it, the computer 194 may prompt the user to input authorization information 750 to establish that the user is authorized to use the electronic cigarette 100. The computer 194 may run a software application that relates to the electronic cigarette 100 and that displays a message prompting the user to input the authorization information 750 via a user interface of the computer 194. As an example, the authorization information 750 may comprise an identifier, such as an alphanumeric identifier (e.g., a passcode) or a biometric identifier. As another example, the authorization information 750 may comprise any other information that is deemed to establish that the user is authorized to vape the electronic cigarette 100. For instance, in some cases, the authorization information 750 may include an indication of the user's age (e.g., a response to a request presented on the user interface of the computer 194 and prompting the user to indicate his/her age or confirm that he/she is at least of a certain age; an answer to a question presented on the user interface of the computer 194 to verify the user's age, etc.).

If the software application running on the computer 194 determines that the authorization information 750 provided by the user is valid, the computer 194 issues an external VCA command to the electronic cigarette 100 in order to enable the vapor-providing capability of the electronic cigarette 100. The external VCA command may be transmitted from the computer 194 to the electronic cigarette 100 via the cable 198 interconnecting them or a wireless connection (e.g., WiFi, Bluetooth, or other wireless connection) interconnecting them. In some cases, the computer 194 may validate the authorization information 750 by comparing it to previously-collected information stored in a memory. In other cases, the computer 194 may send the authentication information 750 to a remote server (e.g., a web server) for validation.

In response to the external VCA command issued by the computer 194, the controller 160 of the electronic cigarette 100 effects a control action in order to enable the vapor-providing capability of the electronic cigarette 100. For instance, the controller 160 may send an internal control signal to the vapor producer 120, the fluid-drawing detector 154, etc., to enable the vapor-providing capability of the electronic cigarette 100.

In a variant, in some embodiments, instead of itself validating the authorization information 750 provided by the user, the computer 194 may relay the authorization information 750 to the controller 160 of the electronic cigarette 100 (e.g., via the cable 198 or wireless connection interconnecting them) and the controller 160 can determine whether the authorization information 750 is valid and, if so, effect a control action in order to enable the vapor-providing capability of the electronic cigarette 100.

In other embodiments, the authorization information 750 to establish that the user is authorized to use the electronic cigarette 100 may be provided in any other suitable way upon recharging of the battery 112 with the charge source 192, including without using the charge source 192 itself.

For example, in some embodiments, the authorization information 750 may be provided via the user interface 150 of the electronic cigarette 100 (e.g., using one or more buttons or other input elements of the input device 156, a particular pattern of drawing on the outlet 152 of the electronic cigarette 100, a biometric sensor, etc.), while the electronic cigarette 100 is connected to the charge source 192 or after the electronic cigarette 100 has been disconnected from the charge source 192. The controller 160 of the electronic cigarette 100 may, upon validating the authorization information 750 provided by the user via the user interface 150, effect a control action in order to enable the vapor-providing capability of the electronic cigarette 100.

As another example, in some embodiments, as shown in FIG. 25, the authorization information 750 may be provided via the mobile communication device 400 (e.g., a smartphone or other wireless phone; a tablet computer; a head-mounted display, smartwatch or other wearable device; etc.) of the user which runs a software application (e.g., a mobile app) that relates to the electronic cigarette 100, while the electronic cigarette 100 is connected to the charge source 192 or after the electronic cigarette 100 has been disconnected from the charge source 192. This may be useful in situations where an individual recharging the electronic cigarette 100 is not authorized to vape the electronic cigarette 100 since, although he/she may have access to the electronic cigarette 100 and the charge source 192, this individual may not have access to the mobile communication device 400.

For instance, while the electronic cigarette 100 is connected to the charge source 192 or upon disconnection of the electronic cigarette 100 from the charge source 192, the controller 160 of the electronic cigarette 100 may send a wireless signal to the mobile communication device 400 to cause the mobile communication device 400 to prompt the user to input the authorization information via the mobile communication device 400. If the software application running on the mobile communication device 400 determines that the authorization information provided by the user is valid, the mobile communication device 400 issues an external VCA command to the electronic cigarette 100 in order to enable the vapor-providing capability of the electronic cigarette 100. Upon receipt of this external VCA command, the controller 160 of the electronic cigarette 100 can effect a control action in order to enable the vapor-providing capability of the electronic cigarette 100.

Similar to what is discussed above in respect of recharging the battery 112 of the electronic cigarette 100, in other embodiments, the depletable resource 184 of the electronic cigarette 100 may be the container 124 of the vapor producer 120 or the substance contained in the container 124 such that the controller 160 of the electronic cigarette 100 monitors the container 124 or the substance contained in the container 124 and, when it determines that the container 124 is being replaced or the substance contained in the container 124 is being replenished, effects a control action to disable the vapor-providing capability of the electronic cigarette 100. The controller 160 may then be attentive to detection of a local VCA event (e.g., receipt of an external VCA command or the authorization information 750 from the user interface 150 of the electronic cigarette 100 or the mobile communication device 400) in order to enable the vapor-providing capability of the electronic cigarette 100.

Example 11

Figure 26:
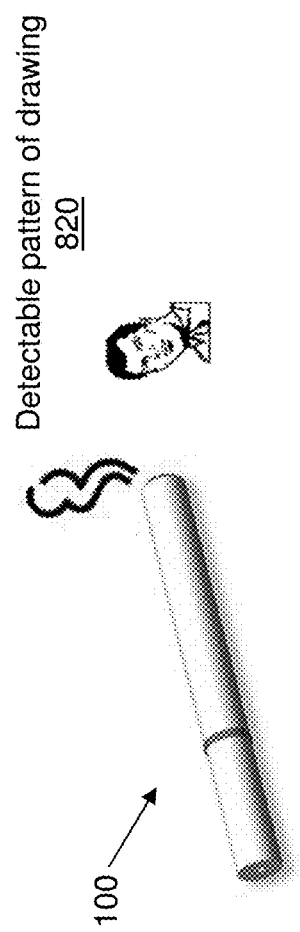

In some embodiments, as shown in FIG. 26, the vapor-providing capability of the electronic cigarette 100 may be altered (e.g., enabled, disabled, etc.) based on a detectable pattern of drawing 820 on the outlet 152 of the electronic cigarette 100 by the user, i.e., a detectable manner in which the user draws on the outlet 152 of the electronic cigarette 100.

For example, in some embodiments, the controller 160 of the electronic cigarette 100 may be responsive to the detectable pattern of drawing 820 on the outlet 152 of the electronic cigarette 100 to enable the vapor-providing capability of the electronic cigarette 100. The vapor-providing capability of the electronic cigarette 100 may be disabled by default (e.g., after a period of time such as 5 or 10 minutes following a last time it was used for vaping) and enabled when the controller 160 detects the detectable pattern of drawing 820 on the outlet 152 of the electronic cigarette 100. The user may thus perform the detectable pattern of drawing 820 on the outlet 152 of the electronic cigarette 100 to "unlock" the electronic cigarette 100. In that sense, the detectable pattern of drawing 820 can be viewed as a fluid-drawing (e.g., inhalation) "passcode" to be carried out by the user in order to be able to vape the electronic cigarette 100.

The detectable pattern of drawing 820 on the outlet 152 of the electronic cigarette 100 constituting the fluid-drawing passcode refers to a pattern of puffs or other draws on the outlet 152 of the electronic cigarette 100 that is detectable by the controller 160 to cause the controller 160 to enable the vapor-providing capability of the electronic cigarette 100. For instance, the detectable pattern of drawing 820 constituting the fluid-drawing passcode may be a series of rapid draws within a short period of time (e.g., three quick puffs within one second), a sequence of longer and shorter puffs within a given period of time (e.g., one long puff followed by two quick puffs within two seconds), or any other suitable detectable pattern of puffs or other draws on the outlet 152 of the electronic cigarette 100.

The controller 160 monitors inputs received from the fluid-drawing detector 154, which detects when the user draws (e.g., puffs, inhales, etc.) fluid through the outlet 152 of the electronic cigarette 100, in order to detect the detectable pattern of drawing 820 on the outlet 152 of the electronic cigarette 100 constituting the fluid-drawing passcode if and when it is performed. These inputs may be indicative of parameters of each draw on the outlet 152 of the electronic cigarette 100, such as a duration of the draw (e.g., how long a pressure differential is sensed by the fluid-drawing detector 154), an intensity of the draw (e.g., a magnitude of the pressure differential sensed by the fluid-drawing detector 154 during the draw), a variation of the intensity of the draw over the duration of the draw (e.g., a pressure vs. time function for the draw), etc. The controller 160 may compare this to information stored in a memory that defines the detectable pattern of drawing 820 on the outlet 152 of the electronic cigarette 100 which is to be recognized by the controller 160 in order to unlock the electronic cigarette 100.

Upon detecting the detectable pattern of drawing on the outlet 152 of the electronic cigarette 100 constituting the fluid-drawing passcode, the controller 160 effects a control action in order to enable the vapor-providing capability of the electronic cigarette 100. For instance, the controller 160 may send an internal control signal to the vapor producer 120, the fluid-drawing detector 154, etc., to enable the vapor-providing capability of the electronic cigarette 100.

Once the user is done vaping the electronic cigarette 100, the controller 160 may determine, based on its monitoring of the fluid-drawing detector 154, that no draw (e.g., inhalation, etc.) on the outlet 152 of the electronic cigarette 100 has occurred in a certain period of time (e.g., 5 or 10 minutes) and may thus effect a control action to disable the vapor-providing capability of the electronic cigarette 100. For instance, the controller 160 may send or refrain from sending an internal control signal to the vapor producer 120, the fluid-drawing detector 154, etc., to disable the vapor-providing capability of the electronic cigarette 100.

The detectable pattern of drawing 820 on the outlet 152 of the electronic cigarette 100 constituting the fluid-drawing passcode that is used to unlock the electronic cigarette 100 may be specified in any suitable way.

For example, in some embodiments, the detectable pattern of drawing 820 on the outlet 152 of the electronic cigarette 100 constituting the fluid-drawing passcode may be specified by a legitimate user (e.g., an owner) of the electronic cigarette 100. In other words, the fluid-drawing passcode to unlock the electronic cigarette 100 may be chosen by the electronic cigarette's legitimate user, which may allow personalization or customization of this passcode. For instance, the legitimate user may interact with the user interface 150 of the electronic cigarette 100 (e.g., using one or more buttons or other input elements of the input device 156) to put the controller 160 in a mode in which it observes inputs received from the fluid-drawing detector 164 while the legitimate user draws on the outlet 152 of the electronic cigarette 100 in a way that defines the detectable pattern of drawing 820 to be subsequently recognized by the controller 160 as the fluid-drawing passcode to unlock the electronic cigarette 100. These inputs may be indicative of parameters of each draw on the outlet 152 of the electronic cigarette 100, such as a duration of the draw (e.g., how long a pressure differential is sensed by the fluid-drawing detector 154), an intensity of the draw (e.g., a magnitude of the pressure differential sensed by the fluid-drawing detector 154 during the draw), a variation of the intensity of the draw over the duration of the draw (e.g., a pressure vs. time function for the draw), etc., that defines the detectable pattern of drawing 820 to be subsequently recognized by the controller 160.

As another example, in some embodiments, the detectable pattern of drawing 820 on the outlet 152 of the electronic cigarette 100 constituting the fluid-drawing passcode that is used to unlock the electronic cigarette 100 may be specified by a manufacturer of the electronic cigarette 100. For instance, the detectable pattern of drawing 820 on the outlet 152 of the electronic cigarette 100 that is to be recognized by the controller 820 may be defined in terms of parameters of each draw that are stored in memory (e.g., a duration of the draw, an intensity of the draw, a variation of the intensity of the draw over the duration of the draw, etc.) by the manufacturer. The detectable pattern of drawing 820 on the outlet 152 of the electronic cigarette 100 may be conveyed to an owner of the electronic cigarette 100, such as by providing a description of the detectable pattern of drawing 820 to be performed to the owner (e.g., as part of documentation provided in packaging of the electronic cigarette 100, by directing the owner to a webpage which provides the description upon entering a serial number or other identifier associated with the electronic cigarette 100, etc.).

In other embodiments, the detectable pattern of drawing 820 on the outlet 152 of the electronic cigarette 100 that is detectable by the controller 160 to alter (e.g., enable, disable, etc.) the vapor-providing capability of the electronic cigarette 100 may be a vaping "signature" that identifies a legitimate user (e.g., an owner) of the electronic cigarette 100. When it determines that a manner of drawing on the outlet 152 of the electronic cigarette 100 does not correspond to the vaping signature, i.e., does not correspond to the detectable pattern of drawing 820 on the outlet 152 of the electronic cigarette 100, the controller 160 proceeds to disable the vapor-providing capability of the electronic cigarette 100. In other words, the controller 160 maintains the electronic cigarette 100 "unlocked" for vaping as long as it detects the vaping signature but "locks" the electronic cigarette 100 to prevent further vaping when it ceases to or otherwise does not detect the vaping signature. An individual who is not the legitimate user identified by the vaping signature recognized by the controller 160 is therefore unlikely to be able to enjoy a prolonged use of the electronic cigarette 100.

The detectable pattern of drawing 820 on the outlet 152 of the electronic cigarette 100 constituting the vaping signature refers to a pattern of puffs or other draws on the outlet 152 of the electronic cigarette 100 that is detectable by the controller 160 to cause the controller 160 to maintain the vapor-providing capability of the electronic cigarette 100 enabled. For instance, the detectable pattern of drawing 820 constituting the vaping signature may be a series of draws of certain durations and/or intensities within a given period of time (e.g., 20 puffs each between 0.6 and 1.2 seconds within an interval of three minutes), a sequence of longer and shorter puffs within a given period of time (e.g., one long puff followed by a shorter puffs within an interval of 30 seconds), or any other suitable detectable pattern of puffs or other draws on the outlet 152 of the electronic cigarette 100.

The controller 160 monitors inputs received from the fluid-drawing detector 154, which detects when the user draws (e.g., puffs, inhales, etc.) fluid through the outlet 152 of the electronic cigarette 100, in order to detect the detectable pattern of drawing 820 on the outlet 152 of the electronic cigarette 100 constituting the vaping signature if and when it is performed. These inputs may be indicative of parameters of each draw on the outlet 152 of the electronic cigarette 100, such as a duration of the draw (e.g., how long a pressure differential is sensed by the fluid-drawing detector 154), an intensity of the draw (e.g., a magnitude of the pressure differential sensed by the fluid-drawing detector 154 during the draw), a variation of the intensity of the draw over the duration of the draw (e.g., a pressure vs. time function for the draw), etc. The controller 160 may compare this to information stored in a memory that defines the detectable pattern of drawing 820 on the outlet 152 of the electronic cigarette 100 which is to be recognized by the controller 160 in order to maintain the vapor-providing capability of the electronic cigarette 100 enabled.

When it detects the detectable pattern of drawing on the outlet 152 of the electronic cigarette 100 constituting the vaping signature, the controller 160 effects a control action in order to maintain the vapor-providing capability of the electronic cigarette 100 enabled. For instance, the controller 160 may send or continue sending an internal control signal to the vapor producer 120, the fluid-drawing detector 154, etc., to maintain the vapor-providing capability of the electronic cigarette 100 enabled.

However, when it ceases to or otherwise does not detect the detectable pattern of drawing on the outlet 152 of the electronic cigarette 100 constituting the vaping signature, the controller 160 effects a control action in order to disable the vapor-providing capability of the electronic cigarette 100. For instance, the controller 160 may send or refrain from sending an internal control signal to the vapor producer 120, the fluid-drawing detector 154, etc., to disable the vapor-providing capability of the electronic cigarette 100.

The detectable pattern of drawing 820 on the outlet 152 of the electronic cigarette 100 constituting the vaping signature that is used to maintain the electronic cigarette 100 unlocked may be specified in any suitable way.

For example, in some embodiments, the detectable pattern of drawing 820 on the outlet 152 of the electronic cigarette 100 constituting the vaping signature may be expressly specified by a legitimate user (e.g., an owner) of the electronic cigarette 100. For instance, the legitimate user may interact with the user interface 150 of the electronic cigarette 100 (e.g., using one or more buttons or other input elements of the input device 156) to put the controller 160 in a mode in which it observes inputs received from the fluid-drawing detector 164 while the legitimate user vapes the electronic cigarette 100 in a way that defines the detectable pattern of drawing 820 to be subsequently recognized by the controller 160 as the vaping signature to maintain the electronic cigarette 100 unlocked. These inputs may be indicative of parameters of each draw on the outlet 152 of the electronic cigarette 100, such as a duration of the draw (e.g., how long a pressure differential is sensed by the fluid-drawing detector 154), an intensity of the draw (e.g., a magnitude of the pressure differential sensed by the fluid-drawing detector 154 during the draw), a variation of the intensity of the draw over the duration of the draw (e.g., a pressure vs. time function for the draw), etc., that defines the detectable pattern of drawing 820 to be subsequently recognized by the controller 160 as the vaping signature of the legitimate user. The parameters defining the vaping signature to be recognized by the controller 160 are stored in a memory of the controller 160.

As another example, in some embodiments, the detectable pattern of drawing 820 on the outlet 152 of the electronic cigarette 100 constituting the vaping signature of a legitimate user (e.g., an owner) of the electronic cigarette 100 may be autonomously learned by the controller 160 of the electronic cigarette 100 by observing how the legitimate user vapes the electronic cigarette 100 over time. For instance, during a predetermined period of time (e.g., a week or month starting from an initial use of the electronic cigarette 100), the controller 160 may observe inputs received from the fluid-drawing detector 164 every time the legitimate user vapes the electronic cigarette 100 and, based on these inputs, identify the detectable pattern of drawing 820 to be subsequently recognized by the controller 160 as the vaping signature to maintain the electronic cigarette 100 unlocked. These inputs may be indicative of parameters of each draw on the outlet 152 of the electronic cigarette 100, such as a duration of the draw (e.g., how long a pressure differential is sensed by the fluid-drawing detector 154), an intensity of the draw (e.g., a magnitude of the pressure differential sensed by the fluid-drawing detector 154 during the draw), a variation of the intensity of the draw over the duration of the draw (e.g., a pressure vs. time function for the draw), etc. For example, based on these inputs, the controller 160 may determine that a particular series of draws on the outlet 152 of the electronic cigarette 100 with certain durations and/or intensities occurs every time the legitimate user vapes the electronic cigarette 100 and may thus define the vaping signature of the legitimate user as being this particular series of draws. The parameters defining the vaping signature to be recognized by the controller 160 are stored in a memory of the controller 160.

Example 12

Figure 27:
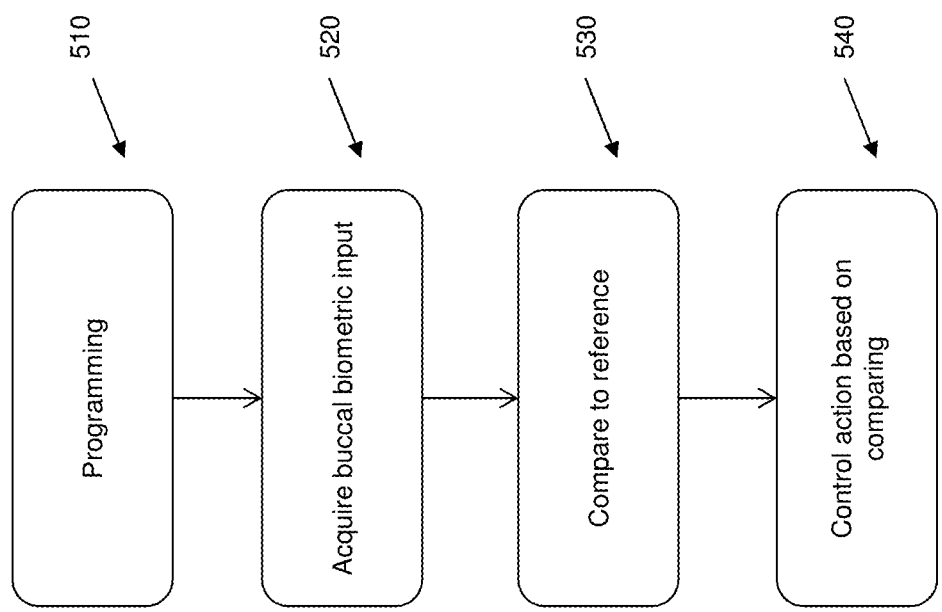

In some embodiments, as shown in FIG. 27, the vapor-providing capability of the electronic cigarette 100 may be altered (e.g., enabled, disabled, etc.) based on buccal biometrics of the user as he/she draws on the outlet 152 of the electronic cigarette 100

To that end, the controller 160 of the electronic cigarette 100 may run a process for acquiring a buccal biometric input 520, comparing the buccal biometric input to a stored buccal biometric reference associated with an authorized user 530, and effecting a control action to alter (e.g., disable) the vapor-providing capability of the electronic cigarette 100 based on a result of the comparing 540. This may be useful, for instance, to reduce a potential for unauthorized use of the electronic cigarette 100, such as would occur if there were an attempted use of the electronic cigarette 100 by someone who is unable to supply recognized buccal biometrics of an authorized user.

Examples of buccal biometric inputs that may be obtained during step 520 include one or more measured features of one or more parts of the user's mouth. Such features may include, for instance: characteristics (e.g., pH, viscosity, hormone levels, DNA, etc.) of biological fluid (e.g., saliva) in the user's mouth; characteristics (e.g., number, position, etc.) of teeth of the user; and/or characteristics (e.g., texture, shape, etc.) of lips of the user, to name a few possibilities. To acquire the buccal biometric input, the electronic cigarette 100 may need to perform measurements on a physical substance (e.g., saliva, jaw, lips, teeth) and thus the electronic cigarette 100 may include components that implement additional functionality.

In one example, the additional functionality for acquiring the buccal biometric input may be provided by an imaging device (e.g., a digital camera) that is mounted to the housing 115 of the electronic cigarette 100 (for taking a picture of the interior of the user's mouth), in combination with image processing software, firmware or hardware, which counts the number and/or position of the user's teeth. There may also be provided a sensor that monitors proximity of the user's mouth so as to trigger the taking of the picture, or the picture may be triggered as soon as the fluid-drawing detector 154 detects that the user is drawing on the outlet 152 of the electronic cigarette 100. In another example, the additional functionality for acquiring the buccal biometric input may be provided by a test system that is mounted to the housing 115 of the electronic cigarette 100 and that enters into contact with fluids in the user's mouth. The test system may be configured to detect a level of one or more hormones present in saliva or another chemical characteristic of the saliva, for example. In yet another example, the additional functionality for acquiring the buccal biometric input may be provided by a pressure sensor that detects a pressure applied by the user's lips.

The buccal biometric reference associated with the authorized user may be obtained during a programming phase 510, during which the controller 160 is programmed to take one or more samples of the buccal biometric input (as described above, for example) and to utilize these samples (or an average thereof) as the buccal biometric reference. In an example, the buccal biometric reference may be reprogrammed by re-entering the programming phase at a later time. During the programming phase, the user of the electronic cigarette 100 is assumed to be the authorized user, and thus it may be of interest to prevent the programming phase from being entered (or re-entered) by an unauthorized user. To this end, a passcode may need to be entered by the user that is attempting to enter (or re-enter) the programming phase.

During the comparing step 530, the buccal biometric input is compared to the buccal biometric reference. In some embodiments, the comparing may be such that the outcome is positive (i.e., a match is declared) only if there is an exact match between the buccal biometric input and the buccal biometric reference. However, in other embodiments, the comparing may produce a positive outcome not only when there is an exact match, but also when there is sufficient similarity between the buccal biometric input and the buccal biometric reference. Similarity may be measured in a variety of ways, such as when the input and reference values are to within a threshold band (e.g., 5%, 10% or 20%) of one another. Other techniques for assessing similarity are possible. For example, a plurality of buccal biometric inputs may be collected and their average may be compared to the buccal biometric reference; alternatively, the one closest to the reference may be the one selected for comparison.

In one example application, where the authorized user is a woman and the woman resides with male children, the mere detection that the saliva of the user is from a male could be a sufficient discriminant to limit the ability of the electronic cigarette 100 to produce vapor and thereby achieve the goal of preventing the children from vaping the electronic cigarette 100.

In another example application, where the authorized user has a certain dentition (including holes, fillings, crowns, etc.), the detection that the user's teeth are different (e.g., lack a crown or filling in an expected position) from those of the authorized user could be used as a trigger to limit the ability of the electronic cigarette 100 to produce vapor, thereby achieving the goal of preventing the user from vaping the electronic cigarette 100.

Example 13

Figure 28:
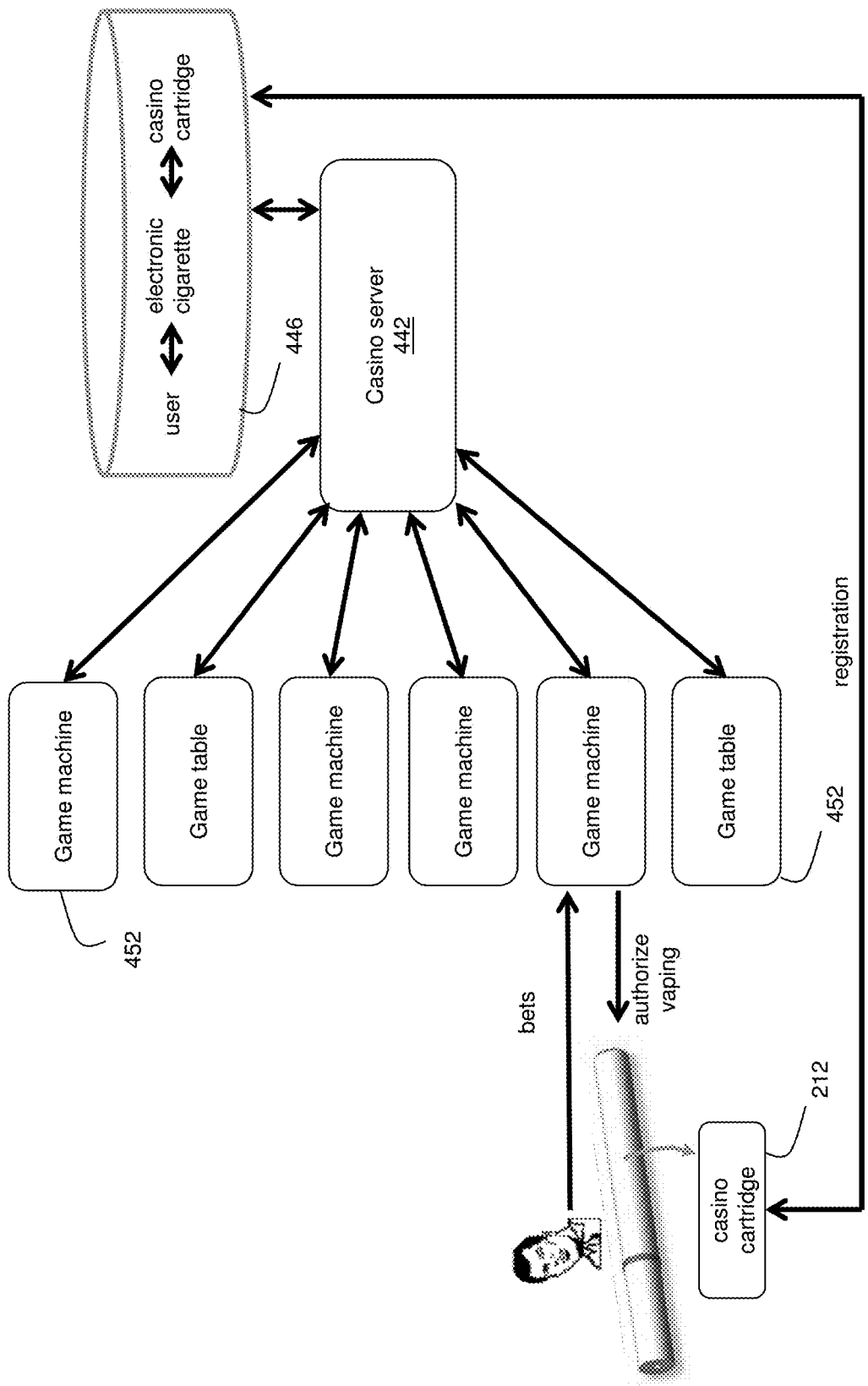

In some embodiments, as shown in FIG. 28, the vapor-providing capability of the electronic cigarette 100 may be altered (e.g., enabled, disabled, etc.) based on a result or progression of game play on a game station in a vicinity of the electronic cigarette 100 (e.g., to allow, enable or facilitate vaping in an arcade or a casino in response to game play).

For example, in some embodiments, upon entry to a casino, patrons are provided with a complimentary "casino cartridge" 212 (e.g., filled with an e-liquid of their choice, flavored or plain, with or without nicotine, alcohol, etc.). The casino cartridge 212 is recognized by the controller 160 of the electronic cigarette 100 as being a casino cartridge and therefore regulated (e.g., requiring a code to operate). As such, the ability of vapor to be produced will only be allowed under certain circumstances. A casino server 442, meanwhile, registers in a database 446 the electronic cigarette 100, the user thereof and the casino cartridge 212. This information may be linked in the form of a database record, for example. As the user plays different games within the casino, the user is recognized by a game station 452, such as a game machine (e.g., slot machine) or a game table (e.g., blackjack table), being played and, depending on the bets placed by the user (either on a single machine or table or cumulatively), the casino server 442 instructs the electronic cigarette 100 (associated with that user) to unblock/enable the casino cartridge 212 and allow vaping (e.g., a limited number of vapes and/or for a limited duration). This can be done by providing a digital key (which may be variable) to the electronic cigarette 100 wirelessly via a nearby gaming apparatus (e.g., game machine or game table). As long as the user keeps up a certain level of betting per unit time (e.g., $100/hr), vaping of the casino cartridge 212 is allowed. However, if the user ceases to bet or slows down, vaping becomes restricted.

The aforementioned technique therefore encourages patrons to continue to play in the casino and indeed bet higher amounts. Different thresholds (of $ bet per unit time so as to enable vaping) can also be applied depending on individuals' gaming profiles. A similar approach can also be used in a video lottery terminal setting or in a traditional arcade, wherein continued spend on machines will lead to authorized access to a complimentary source of vaping.

Other venues for controllably encouraging vaping of e-fluid based on consumer behavior may include department stores, restaurants, shopping malls, grocery stores and other locations where prolonged user presence is linked with increased consumer spend.

In some embodiments, certain functionality implemented by the communication device 400 in the examples considered above, such as, for instance, monitoring the location of the electronic cigarette 100, monitoring a time of day, monitoring the vaping activity, knowing the location of a vaping-prohibited area, etc., may instead be implemented by the electronic cigarette 100 itself. That is, the controller 160 of the electronic cigarette 100 may interact with other components of the electronic cigarette 100 (e.g., a GPS locator, a clock, a memory storing locations of vaping-prohibited areas, etc.) in order to implement this functionality.

Alternatively or in addition, in some embodiments, the user interface 150 of the electronic cigarette 100 may implement a graphical user interface providing a function for allowing the user to input an external VCA command, which causes the vapor-providing capability of the electronic cigarette 100 to be altered without shutting down the electronic cigarette 100.

II. Conveyance of a Notification of Potential Unauthorized Use

Figure 29:
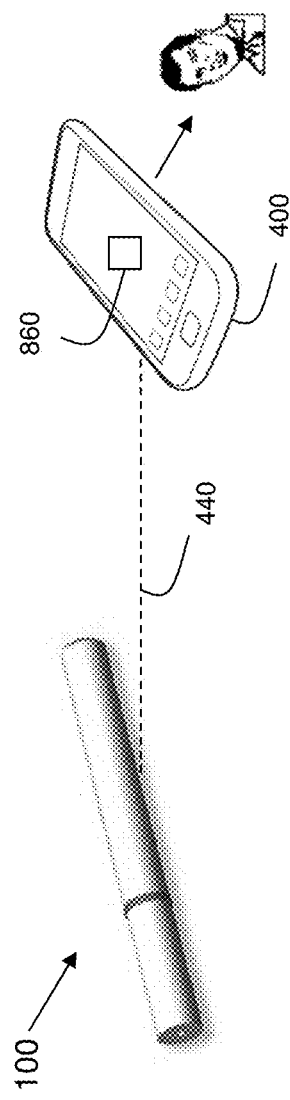
FIG. 29 shows an example of a notification of potential unauthorized use of the electronic vaping device.

In some embodiments, as shown in FIG. 29, the electronic cigarette 100 may communicate with the communication device 400 (e.g., a smartphone, a computer, etc.) that is external to the electronic cigarette 100 to convey a notification 860 of potential unauthorized use of the electronic cigarette 100 (e.g., by a child, teenager or other unauthorized user). This notification 860, which will be referred to as a "potential unauthorized use (PUU) notification", may be useful, for instance, to notify an authorized user (e.g., an owner) of the electronic cigarette 100 that the electronic cigarette 100 may potentially be used by an unauthorized user, such as a child or teenager who is not allowed to vape or an individual who may have stolen the electronic cigarette 100 or have found the electronic cigarette 100 if forgotten or misplaced by the authorized user.

For example, in this embodiment, the communication device 400 is a mobile communication device (e.g., a smartphone or other wireless phone; a tablet computer; a head-mounted display, smartwatch or other wearable device; etc.) of the authorized user who is an owner of the electronic cigarette 100. In this case, the mobile communication device 400 runs a software application (e.g., a mobile app) that is related to the electronic cigarette 100 and that can deliver the PUU notification 860. In other cases, the mobile communication device 400 may be able to deliver the PUU notification 860 without running any software application related to the electronic cigarette 100 (e.g., the PUU notification 860 may be delivered as a text message (e.g., SMS message) or an email message presentable by the mobile communication device 400).

The PUU notification 860 may be implemented in any suitable way. For example, in some embodiments, the PUU notification 860 may include a visual element displayed on a display of the mobile communication device 400 (e.g., a pop-up window conveying a textual message, an email message, a text message, etc.). As another example, in some embodiments, the PUU notification 860 may include an audible element emitted by a speaker of the mobile communication device 400 (e.g., an audio warning). As yet another example, in some embodiments, the PUU notification 860 may include both a visual element and an audible element.

The PUU notification 860 is issued in response to an event indicative of potential unauthorized use of the electronic cigarette 100. This event, which will be referred to as a "PUU event", may include one or more conditions being met (e.g., one or more circumstances having arisen) in respect of the electronic cigarette 100. Any or all of these one or more conditions may be predefined or otherwise specified such that, when the one or more conditions are met, the PUU event is deemed to have occurred.

Detection that the one or more conditions are met in respect of the electronic cigarette 100, and therefore detection of a PUU event, may be carried out by the electronic cigarette 100 and/or by a communication device external to the electronic cigarette 100 such as the mobile communication device 400. At the electronic cigarette 100, this may be achieved based on processing of one or more inputs that may be received by the controller 160 of the electronic cigarette 100. Examples of such inputs may include external inputs received via the user interface 150 and/or the communication interface 170 and/or internal inputs from various internal components (e.g., a clock, a GPS locator, a battery, etc.) of the electronic cigarette 100. At a communication device external to the electronic cigarette 100 such as the mobile communication device 400, this may be carried out by processing circuitry at the external communication device that takes into account one or more stimuli. Examples of such stimuli may include external inputs received via a user interface and/or a communication interface of the external communication device and/or internal inputs from various internal components (e.g., a clock, a GPS locator, a battery, etc.) of the external communication device.

The PUU event which triggers issuance of the PUU notification 860 may be defined by one or more conditions (e.g., circumstances) that may involve various factors, including, for example, one or more of:

a location of the electronic cigarette 100 (e.g., to notify of potential authorized use when there is a lack of proximity of the electronic cigarette 100 to its owner, when the electronic cigarette 100 is no longer located in a home, workplace, or other site associated with its owner, etc.);

time (e.g., to notify of potential authorized use when the electronic cigarette 100 is activated at certain times of day or other specified moments during which the owner of the electronic cigarette 100 is not expected to vape the electronic cigarette 100); and/or an indication of a desire of the owner of the electronic cigarette 100 to be notified of an upcoming use of the electronic cigarette 100 (e.g., within a certain period of time, such as an upcoming day, week or month to learn of any authorized use of the electronic cigarette 100 that may occur during that period of time);

etc.

For instance, in some embodiments, the owner of the electronic cigarette 100 may specify one or more conditions (e.g., circumstances) under which he/she wishes to receive the PUU notification 860 via his/her mobile communication device 400. This may be achieved by the owner of the electronic cigarette 100 providing user input defining these one or more conditions via the input device 156 of the user interface 150 of the electronic cigarette 100 and/or via the user input of the mobile communication device 400.

As an example, the owner of the electronic cigarette 100 may specify that he/she wishes to be notified when the electronic cigarette 100 ceases to be in proximity of the mobile communication device 400. For instance, the software application running on the mobile communication device 400 may monitor a proximity of the mobile communication device 400 to the electronic cigarette 100 in order to issue the PUU notification 860 when the electronic cigarette 100 is deemed to no longer be proximate enough to the mobile communication device 400, which is presumed to be with the owner of the electronic cigarette 100. It should be appreciated that proximity may be assessed in various ways, such as by comparing the actual location of the mobile communication device 400 to that of the electronic cigarette 100, or by detecting a distance (e.g., based on signal strength, signal travel time, etc.) between the mobile communication device 400 and the electronic cigarette 100, to name a few possibilities. Thus, when the software application determines that the mobile communication device 400 and the electronic cigarette 100 are not within a specified distance (e.g., 1 or 2 m) from one another, the mobile communication device 400 issues the PUU notification 860 which can notify the owner of the electronic cigarette 100 of this situation.

As another example, the owner of the electronic cigarette 100 may specify that he/she wishes to be notified when the electronic cigarette 100 is being vaped while not in proximity of the mobile communication device 400, which is presumed to be with him/her. For instance, the controller 160 of the electronic cigarette 100 may monitor a proximity of the electronic cigarette 100 to the mobile communication device 400 and, when the electronic cigarette 100 is deemed by the controller 160 to no longer be proximate enough to the mobile communication device 400, the controller 160 monitors inputs received from the fluid-drawing detector 154 to determine whether someone has drawn (e.g., puffed, inhaled, etc.) on the outlet 152 of the electronic cigarette 100. If the controller 160 detects that someone has drawn on the outlet 152 of the electronic cigarette 100 while it is not in proximity to the mobile communication device 400, the controller 160 causes transmission of a signal over the communication link 440 to issue the PUU notification 860 at the mobile communication device 400 in order to notify the owner of the electronic cigarette 100 of this situation.

As yet another example, the owner of the electronic cigarette 100 may specify that he/she wishes to be notified when the electronic cigarette 100 is being vaped during a predetermined period of time, say between 12 PM and 6 AM during which time he/she normally sleeps. For instance, the controller 160 of the electronic cigarette 100 may monitor a time of day and inputs received from the fluid-drawing detector 154 to determine whether someone has drawn (e.g., puffed, inhaled, etc.) on the outlet 152 of the electronic cigarette 100 between 12 PM and 6 AM. If the controller 160 detects that someone has drawn on the outlet 152 of the electronic cigarette 100 during that time, the controller 160 causes transmission of a signal over the communication link 440 to issue the PUU notification 860 at the mobile communication device 400 in order to notify the owner of the electronic cigarette 100 of this situation.

In some embodiments, the PUU notification 860 may be conveyed via the mobile communication device 400 in conjunction with an alteration (e.g., a disabling, a reduction, etc.) of the vapor-providing capability of the electronic cigarette 100 as discussed above in section I. Thus, the owner of the electronic cigarette 100 may, in addition to being notified of the potential unauthorized use of the electronic cigarette 100, know that the vapor-providing capability of the electronic cigarette 100 is being disabled, reduced or otherwise altered such that it cannot be used normally.

In some examples, the alteration (e.g., disabling, reduction, etc.) of the vapor-providing capability of the electronic cigarette 100 as discussed above in section I may be effected automatically along with issuance of the PUU notification 860 via the mobile communication device 400. For instance, in some cases, in conjunction with issuance of the PUU notification 860 via the mobile communication device 400, the controller 160 of the electronic cigarette 100 may send or refrain from sending an internal control signal to the vapor producer 120, the fluid-drawing detector 154, etc., to disable the vapor-providing capability of the electronic cigarette 100.

In other examples, the alteration (e.g., disabling, reduction, etc.) of the vapor-providing capability of the electronic cigarette 100 as discussed above in section I may be effected in response to the owner of the electronic cigarette 100 inputting a command to effect this alteration via the user interface of the mobile communication device 400 upon having received the PUU notification 860 conveyed via the mobile communication device 400. For instance, the software application running on the mobile communication device 400 may, upon receiving the PUU notification 860, provide an option for the owner of the electronic cigarette 100 to alter (e.g., disable, reduce, etc.) the vapor-providing capability of the electronic cigarette 100. The option may be provided by displaying a message or other graphical element on the display of the communication device 400 that prompts the owner of the electronic cigarette 100 to indicate whether he/she would like to disable, reduce or otherwise alter the vapor-providing capability of the electronic cigarette 100 and that can be acted upon by the owner of the electronic cigarette 100 (e.g., by clicking on a button or other actionable element) of the user interface of the mobile communication device 400. The owner of the electronic cigarette 100 may thus interact with the mobile communication device 100 to specify that he/she wants to disable, reduce or otherwise alter the vapor-providing capability of the electronic cigarette 100 and cause the mobile communication device 100 to send an external VCA command towards the electronic cigarette 100 over the communication link 440 such that, upon receiving this external VCA command, the controller 160 of the electronic cigarette 100 effects a control action in order to disable, reduce or otherwise alter the vapor-providing capability of the electronic cigarette 100. For instance, the controller 160 may send or refrain from sending an internal control signal to the vapor producer 120, the fluid-drawing detector 154, etc., to disable, reduce or otherwise alter the vapor-providing capability of the electronic cigarette 100.

In other embodiments, the PUU notification 860 may be conveyed via the mobile communication device 400 without altering (e.g., disabling, reducing, etc.) the vapor-providing capability of the electronic cigarette 100 as discussed above in section I.

III. Physical Deterrence to Unauthorized Use

Figure 30:
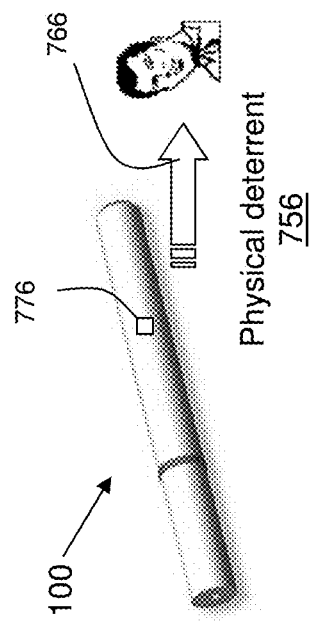
FIG. 30 shows an example of a physical deterrent implemented by the electronic vaping device to deter its unauthorized use.

In some embodiments, as shown in FIG. 30, the electronic cigarette 100 may implement a physical deterrent 756 to its unauthorized use (e.g., by a child, teenager or other unauthorized user)

For example, in this embodiment, the physical deterrent 756 constitutes emission of a sensory artefact 766 (e.g., sound, odor, light) that certain users other than an authorized user (e.g., an owner) of the electronic cigarette 100 would likely find unpleasant. In this embodiment, the ability of the electronic cigarette 100 to produce vapor is not limited.

To that end, the electronic cigarette 100 may be equipped with an artefact producer 776 which is activated by the controller 160 of the electronic cigarette 100. Activation of the artefact producer 776 may be continuous or in response to an event, such as drawing on the outlet 152 of the electronic cigarette 100 after a prolonged period (e.g., 15, 30 or 60 minutes, or more) of not having drawn on the outlet 152. The artefact producer 776 may produce the sensory artefact 766 that certain users other than the authorized user would likely find unpleasant. For example, when the authorized user is hard of hearing, producing a shrill or high-pitched sound, or playing overplayed Christmas music, may discourage unauthorized users who begin to use the electronic cigarette 100 from continuing to use the electronic cigarette 100. Similarly, when the authorized user is an adult above 25 years of age, producing sounds above 17.4 kHz would be inaudible to the authorized user, yet audible by individuals younger than 24 and certainly children. In this way, a continuous or variable sound in a desired frequency range that is produced in response to, say, drawing on the electronic cigarette 100 (as detected by the fluid-drawing detector 154), may discourage unauthorized users from using the electronic cigarette 100. Of course, other frequencies may be applicable to other age groups, where individuals in the age group of an authorized user may be unaffected by sounds audible by individuals in a different age group to which unauthorized users belong.

In yet another example, the artefact producer 776 may produce other sensory artefacts such as customized scents to which the authorized user is unlikely to object, yet would be found repulsive by unauthorized users. Examples of scents include those arising from various secretions of sweat or pubic glands, or gaseous emissions from the mouth. Such scents may be obtained from natural concentrations or they may chemically synthesized.

In still another example, the artefact producer 776 may produce light patterns or signals that would be found annoying or unpleasant by an unauthorized user. For example, a visual output device (e.g., a visual output device 190 in FIGS. 31 and 32, described in greater detail later) built into the housing 150 of the electronic cigarette 100 may display a certain color or message (e.g., "unauthorized user") when the user is an unauthorized user. Thus, although use of the electronic cigarette 100 may not be physically prevented or inhibited, it is discouraged indirectly through the discomfort that the user would be led to feel when those around him or her are alerted to the fact that the use is unauthorized.

This embodiment may therefore be useful in reducing the potential for unauthorized use of the electronic cigarette 100, such as would occur if there were an attempted use of the electronic cigarette 100 by someone who lacks the stamina to endure the emitted sensory artefacts.

IV. Visual Conveyance of Information

Figure 31:
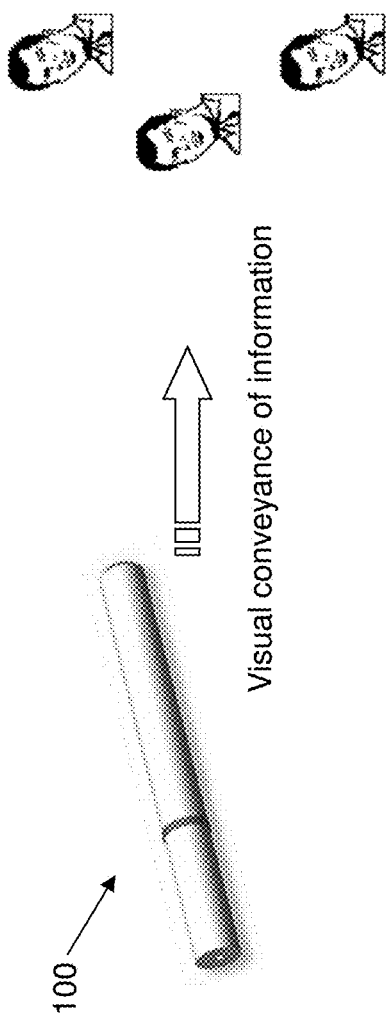
FIGS. 31 and 32 show an example of visual conveyance of information by the electronic vaping device.
Figure 32:
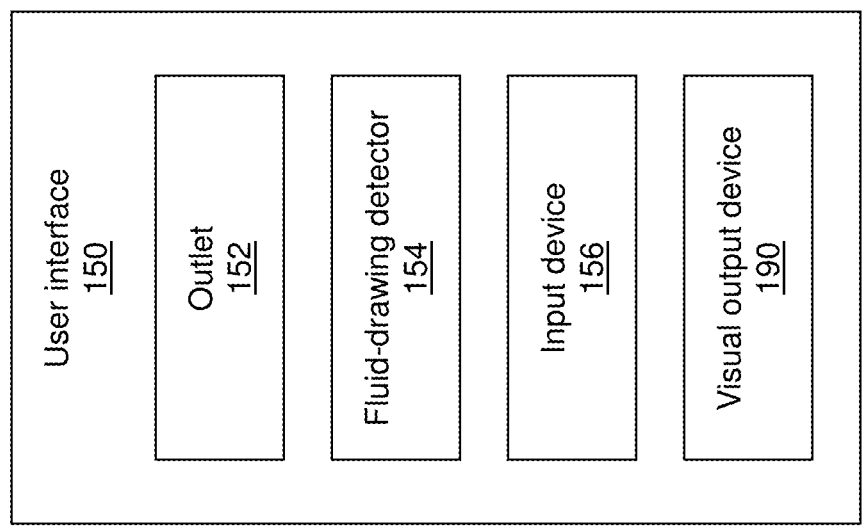

In some embodiments, as shown in FIGS. 31 and 32, the user interface 150 of the electronic cigarette 100 may comprise a visual output device 190 to convey information visually to the user and/or one or more other individuals in the vicinity of the electronic cigarette 100 who can see the electronic cigarette 100. For example, in some embodiments, the visual output device 190 may include a controllably-illuminated tip of the electronic cigarette 100 (e.g., an LED or other light source whose light emission is controllable). As another example, in some embodiments, the visual output device 190 may include an electronic display (e.g., a LCD screen, an OLED screen, etc.), which may be configured for displaying text, graphics and/or video. In some cases, the electronic display may be curved and/or flexible, and may appear on a side of the housing 115 of the electronic cigarette 100.

Causing the electronic cigarette 100 to visually convey information may be useful, for instance, to:
  present information entered by the user in real-time to individuals in the vicinity of the electronic cigarette 100;
  present advertisements (e.g., for companies or other organizations, products, services, etc.) or other messages to people who can see the electronic cigarette 100;

notify people in the vicinity of the electronic cigarette 100 that it is not a conventional cigarette (e.g., by blinking or otherwise controlling illumination of a tip of the electronic cigarette 100 to indicate that it is not something burning, by flashing or otherwise altering any data on a display of the electronic cigarette 100, etc.);

present personal information (e.g., name, social/relationship status, etc.) of the user or other information stored in a database or profile (e.g., which may be online, such as a social media account);

show electronic messages (e.g., text messages or email messages) received on a communication device of the user; and/or notify people in the vicinity of the electronic cigarette 100 that a current use of the electronic cigarette 100 is unauthorized (e.g., if the electronic cigarette 100 is used by someone who is unauthorized to use it, such as a child or someone who stole or found the electronic cigarette 100);

etc.

The information visually conveyed by the visual output device 190 may include (1) information received by the electronic cigarette 100 from an external source ("externally received information") and/or (2) information inherent to the electronic cigarette 100 (e.g., the fact that the electronic cigarette 100 is not a traditional cigarette).

In the case of externally received information that is to be conveyed by the electronic cigarette 100, this information may be received in various ways, including, for example, those discussed below.

1—Direct

In the direct technique, the input device 156 of the user interface 150 of the electronic cigarette 100 (e.g., including one or more buttons, a touch screen and/or any other input mechanism) allows the user to directly enter (e.g., select or input) the information to be visually conveyed by the visual output device 190 of the electronic cigarette 100.

2—Paired

In the paired technique, a specific communication device (or a group of specific communication devices) is paired with the electronic cigarette 100, such that only signals received from the specific communication device (or the group of specific communication devices) are recognized as valid. The specific communication device can be a smartphone or other mobile phone, a tablet, a smart watch, head-mounted display or other wearable device, etc., or even another electronic cigarette.

For example, in some embodiments, the user may download an application (app) from a repository (e.g., Apple's App Store, iTunes, Google Play, Android Market, etc.) onto the specific communication device that is paired with the electronic cigarette 100. Upon activation of the app on the specific communication device, the user may access certain features to control certain aspects of the electronic cigarette 100 (including output of information by the visual output device 190 of the electronic cigarette 100) locally on the specific communication device. This can be achieved by sending a command from the specific communication device to the electronic cigarette 100. In addition, a data connection can be established over the Internet with a server of which executes a complementary server-side application interacting with the app on the specific communication device.

3—Addressed

In the addressed technique, the electronic cigarette 100 is assigned a network identifier, such as an IP address, and is able to communicate over a network with other devices having IP addresses. As such, knowledge of the electronic cigarette's IP address allows other networked devices to communicate with the electronic cigarette 100. Such communication may include transmission of information to be visually conveyed by the visual output device 190 of the electronic cigarette 100.

4—Out-of-Band

In the out-of-band technique, a communication channel is reserved for emergency or administrative use rather than data communication with other networked devices. For example, this could include a reserved frequency (in the case of an FDMA system), a reserved multiplexing code (in the case of a CDMA system), a reserved time slot (in the case of a TDMA system), a reserved encryption key (in the case of a digital system) or a reserved network identifier (e.g., IP address). This can allow operational control of the electronic cigarette 100 to be overridden and controlled by an external entity, such as in an emergency or where mandated by law.

In case 1 identified above, the information to be visually conveyed by the electronic cigarette 100 is provided by the user.

In each of cases 2, 3 and 4 identified above, the information to be visually conveyed by the electronic cigarette 100 is issued by a communication device that is external to the electronic cigarette 100 and conveyed via a communication link, which may be wireless, wired, or partly wireless and partly wired (e.g., Bluetooth, WiFi or other wireless LAN, WiMAX or other wireless WAN, cellular, USB, etc.), such as the communication device 400 and the communication link 440 discussed above in connection with FIG. 7. For example: in the paired technique, the communication device 400 may be a smartphone or other mobile phone, a tablet, a smart watch, head-mounted display or other wearable device, or any other communication device that may be carried by the user, and the communication link 440 may a short-range wireless link (e.g., Bluetooth) or a wired link (e.g., USB); in the addressed technique, the communication device 400 may be a server or other computing apparatus or a smartphone or other mobile phone, a tablet, a smart watch, head-mounted display or other wearable device, or any other communication device that may be carried by the user and the communication link 440 may be implemented by a data network such as the Internet over a wired connection and/or a wireless connection (e.g., WiFi, WiMAX, cellular, etc.); and, in the out-of-band technique, the communication device 400 may be a server or other computing apparatus and the communication link 440 may be implemented over a wireless connection using, for instance, dedicated short-range communication (DSRC), IEEE 802.11, Bluetooth and CALM (Communications Access for Land Mobiles), RFID, etc.

Release of the information to be visually conveyed by the electronic cigarette 100 may be caused by a program (e.g., a software application) executing on the communication device 400. The program may include a set of computer-readable instructions executed by a processor of the communication device 400. The computer-readable instructions may be stored in a memory embedded in the communication device 400 or located externally thereto. The algorithm takes into one or more stimuli, which can include external inputs received via a user interface of the communication device 400, external inputs received via a communication interface of the communication device 400 and/or internal inputs from various internal components of the communication device 400 (e.g., a clock, a GPS locator, a battery, etc.).

The program executing on the communication device 400 may determine what information is to be visually conveyed by the electronic cigarette 100 based on various factors, such as, for example:

- input from the user of the electronic cigarette 100 or another individual (e.g., a person who may interact with the communication device 400 in cases where the communication device 400 is not under control of the user of the electronic cigarette 100);
- a state of the electronic cigarette 100 (e.g., currently or not currently being used to vape);
- an identity of the user (e.g., an age of the user);
- a location of the electronic cigarette 100 (e.g., to display advertisements for nearby stores, restaurants, or other merchants in a targeted manner);
- time;
- etc.

In some embodiments, the controller 160 of the electronic cigarette 100 may cause the visual output device 190 to visually convey information by the electronic cigarette 100 upon determining that the electronic cigarette 100 is currently being used to vape or otherwise positioned such that the information is viewable by the user and/or individuals in the vicinity of the electronic cigarette 100. For example, in some cases, the controller 160 may monitor the fluid-drawing detector 154 to make this determination. As another example, in some cases, the electronic cigarette 100 may comprise a motion sensor (e.g., including a gyroscope or accelerometer) to sense motion of the electronic cigarette 100 and the controller 160 may monitor the motion sensor to assess whether the electronic cigarette 100 is positioned (e.g., oriented) in a way that it is viewable by the user and/or individuals in the vicinity of the electronic cigarette 100.

In examples where the information visually conveyed by the electronic cigarette 100 includes an advertisement (e.g., for a company or other organization, a product, or a service), this may be subsidized by an advertiser who may compensate the user of the electronic cigarette 100 for allowing the advertisement to be presented via the electronic cigarette 100.

For example, in some embodiments, the user may have subscribed to or registered for an advertisement service provided by the advertiser or otherwise have given his/her consent to the advertiser to convey the advertisement via the electronic cigarette 100. In some embodiments, this may be achieved, for example, by the user interacting (e.g., using the electronic cigarette 100 itself, or using his/her smartphone, tablet, laptop computer, etc.) with a server (e.g., implementing a website) that is associated with the advertiser and allows the user to consent to presentation of advertisements on the electronic cigarette 100. The server may maintain a record (e.g., an account) for the electronic cigarette 100 and keep track of advertisements presented on the electronic cigarette 100.

Compensation to the user of the electronic cigarette 100 for allowing the advertisement to be conveyed on the electronic cigarette 100 may be in any suitable form. For example, in some embodiments, the user may receive a financial compensation (e.g., an amount of money deposited in a bank account, a credit applicable towards a purchase, a rebate on a product or service advertised, etc.). This compensation may be managed by the server associated with the advertiser.

V. Capturing of Images and/or Sounds

Figure 33:
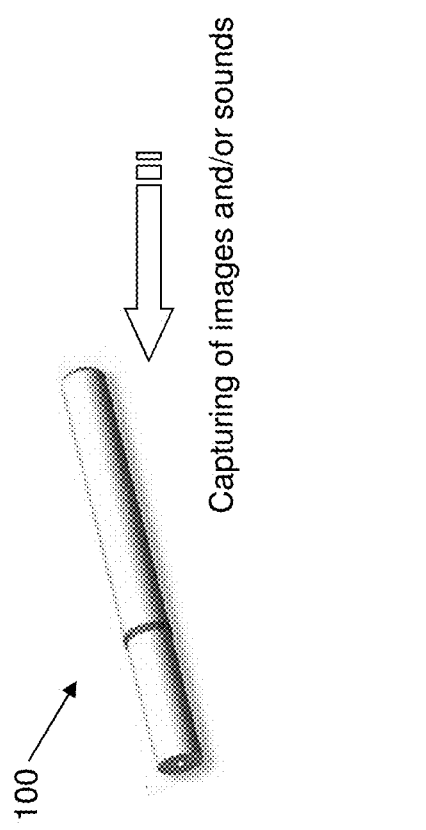
FIGS. 33 and 34 show an example of capturing of images and/or sounds by the electronic vaping device.
Figure 34:
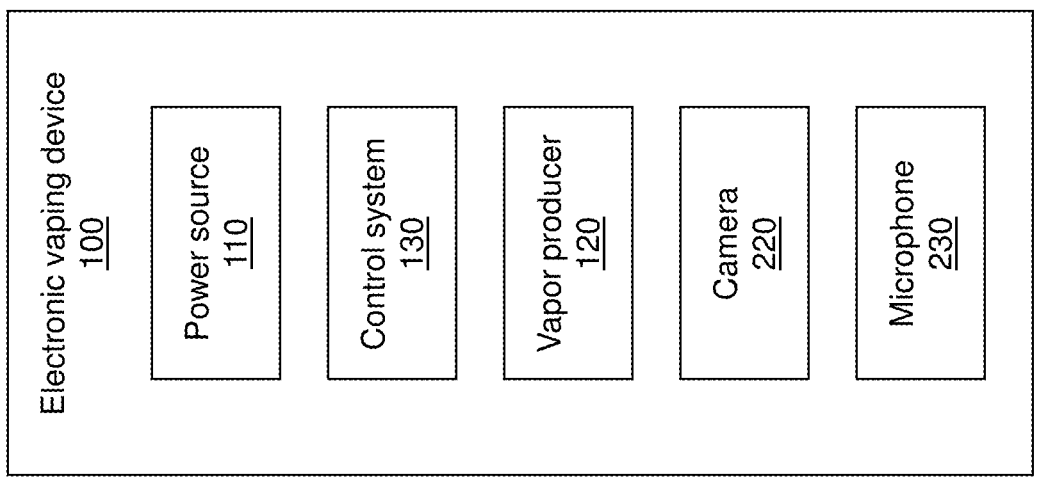

In some embodiments, as shown in FIGS. 33 and 34, the electronic cigarette 100 may comprise one or more media-capturing devices to capture media, i.e., images and/or sounds (e.g., of surroundings of the electronic cigarette 100). For instance, the electronic cigarette 100 may comprise a camera 220 to capture images. In some cases, the images captured by the camera 220 may include pictures (i.e., still images). In other cases, the camera 220 may have video capability such that the images it captures include moving images constituting video. The electronic cigarette 100 may also comprises a microphone 230 to capture sounds (e.g., particularly in cases where the camera 220 has video capability).

This ability of the electronic cigarette 100 to capture images and/or sounds may be useful, for instance, to:

- allow the user of the electronic cigarette 100 to conveniently and discreetly take pictures or videos when desired (e.g., when vaping, without having to simultaneously handle or manipulate his/her smartphone or digital camera, etc.);
- allow automatic upload of pictures or videos taken by the electronic cigarette 100 to a third-party site via a wireless connection (e.g., a site associated with a manufacturer of the electronic cigarette 100 for a promotional campaign (e.g., "show us where you vape" campaign), distributed on social media, etc.);
- allow continuous surveillance around the electronic cigarette 100 (e.g., a security feature for a woman in a bar who wants to record potentially predatory behaviour); and/or
- etc.

Images and/or sounds may be captured by the electronic cigarette 100 in various ways in various embodiments, including those discussed below.

1—Direct

In the direct technique, the input device 156 of the user interface 150 of the electronic cigarette 100 (e.g., including one or more buttons, a touch screen and/or any other input mechanism) allows the user to directly input a command to take a picture or video. In response to such a command from the user, the controller 160 causes the camera 220 to capture a picture or video. In cases where a video is taken, the microphone 230 is caused by the controller 160 to capture associated audio content.

2—Paired

In the paired technique, a specific communication device (or a group of specific communication devices) is paired with the electronic cigarette 100, such that only signals received from the specific communication device (or the group of specific communication devices) are recognized as valid. The specific communication device can be a smartphone or other mobile phone, a tablet, a smart watch, head-mounted display or other wearable device, etc., or even another electronic cigarette.

For example, in some embodiments, the user may download an application (app) from a repository (e.g., Apple's App Store, iTunes, Google Play, Android Market, etc.) onto the specific communication device that is paired with the electronic cigarette 100. Upon activation of the app on the specific communication device, the user may access certain features to control certain aspects of the electronic cigarette 100 (including taking a picture or video with the camera 220) locally on the specific communication device. This can be achieved by sending a command from the specific communication device to the electronic cigarette 100. In addition, a data connection can be established over the Internet with a server of which executes a complementary server-side application interacting with the app on the specific communication device.

3—Addressed

In the addressed technique, the electronic cigarette 100 is assigned a network identifier, such as an IP address, and is able to communicate over a network with other devices having IP addresses. As such, knowledge of the electronic cigarette's IP address allows other networked devices to communicate with the electronic cigarette 100. Such communication may include transmission of a command to take a picture or video with the camera 220 of the electronic cigarette 100.

4—Out-of-Band

In the out-of-band technique, a communication channel is reserved for emergency or administrative use rather than data communication with other networked devices. For example, this could include a reserved frequency (in the case of an FDMA system), a reserved multiplexing code (in the case of a CDMA system), a reserved time slot (in the case of a TDMA system), a reserved encryption key (in the case of a digital system) or a reserved network identifier (e.g., IP address). This can allow operational control of the electronic cigarette 100 to be overridden and controlled by an external entity, such as in an emergency or where mandated by law.

5—Vape-Activated

In the vape-activated technique, the electronic cigarette 100 can take a picture or video in response to a vaping action of the user. More particularly, the electronic cigarette 100 may autonomously take a picture or video in response to the user drawing on the outlet 152 of the electronic cigarette 100. For example, in some embodiments, the electronic cigarette 100 may take a picture or video at each draw (e.g., inhalation or puff) made by the user on the outlet 152 of the electronic cigarette 100. As another example, in some embodiments, the electronic cigarette 100 may take a picture or video in response to a triggering pattern of drawing by the user on the outlet 152 of the electronic cigarette 100 (e.g., a series of rapid draws within a short period of time, such as 3 quick puffs within 2 seconds). The controller 160 may interact with the fluid-drawing detector 154 to detect when the user draws on the outlet 152 of the electronic cigarette 100 and cause the camera 220 to take a picture or video accordingly.

In case 1 identified above, the command to take a picture or video with the electronic cigarette 100 is provided by the user.

In each of cases 2, 3 and 4 identified above, the command to take a picture or video with the electronic cigarette 100 is issued by a communication device that is external to the electronic cigarette 100 and conveyed via a communication link, which may be wireless, wired, or partly wireless and partly wired (e.g., Bluetooth, WiFi or other wireless LAN, WiMAX or other wireless WAN, cellular, USB, etc.), such as the communication device 400 and the communication link 440 discussed above in connection with FIG. 7. For example: in the paired technique, the communication device 400 may be a smartphone or other mobile phone, a tablet, a smart watch, head-mounted display or other wearable device, or any other communication device that may be carried by the user, and the communication link 440 may a short-range wireless link (e.g., Bluetooth) or a wired link (e.g., USB); in the addressed technique, the communication device 400 may be a server or other computing apparatus or a smartphone or other mobile phone, a tablet, a smart watch, head-mounted display or other wearable device, or any other communication device that may be carried by the user and the communication link 440 may be implemented by a data network such as the Internet over a wired connection and/or a wireless connection (e.g., WiFi, WiMAX, cellular, etc.); and, in the out-of-band technique, the communication device 400 may be a server or other computing apparatus and the communication link 440 may be implemented over a wireless connection using, for instance, dedicated short-range communication (DSRC), IEEE 802.11, Bluetooth and CALM (Communications Access for Land Mobiles), RFID, etc.

Release of the command to take a picture or video with the electronic cigarette 100 may be caused by a program (e.g., a software application) executing on the communication device 400. The program may include a set of computer-readable instructions executed by a processor of the communication device 400. The computer-readable instructions may be stored in a memory embedded in the communication device 400 or located externally thereto. The algorithm takes into one or more stimuli, which can include external inputs received via a user interface of the communication device 400, external inputs received via a communication interface of the communication device 400 and/or internal inputs from various internal components of the communication device 400 (e.g., a clock, a GPS locator, a battery, etc.).

The images and/or sounds captured by the electronic cigarette 100 may be stored in a memory of the electronic cigarette 100. Alternatively or additionally, the images and/or sounds captured by the electronic cigarette 100 may be transmitted to one or more external communication devices (e.g., the communication device 400 and/or one or more additional communication devices, such as a server managing a social media account of the user, etc.).

VI. Usage Monitoring

In some embodiments, usage of the electronic cigarette 100 may be monitored by a software application. This may include monitoring vaping of the electronic cigarette 100 and/or monitoring of replacement of the container 124 of the vapor producer 120 or replenishment of the substance contained in the container 124. Information derived from this monitoring may then be used for various purposes in various embodiments, such as, for example, to:

a) monitor overall vaping (e.g., consumption, habits, etc.) across the electronic cigarette 100 and one or more other electronic cigarettes registered to the same user;

b) transfer data stored in association with the electronic cigarette 100 from a previously-used electronic cigarette and/or to a new electronic cigarette;

c) detect tampering with the electronic cigarette 100, such as by logging the times at which the electronic cigarette 100 was opened and/or closed and then advising the user of these times, since the user who knows when they last opened the electronic cigarette 100 (to replace the container 124 or replenish the substance it contains) could therefore know whether the electronic cigarette 100 was opened by someone else, which could signal tampering;

d) determine the user's usage rate by logging the time instants at which the electronic cigarette 100 was vaped (e.g., this may be transmitted to a server which computes rate of vaping and rewards the "high score" (daily or monthly) with cash or prizes);

e) determine the user's true loyalty to a brand by logging the brand of each new cartridge that is installed in the electronic cigarette 100, and, if loyal to a particular brand of cartridge, the user may be rewarded.

In various embodiments, a communications link mentioned herein may be implemented by a data network (e.g., the Internet), a public telephony network (e.g., the PSTN), and/or a wireless network (e.g., a cellular network, a satellite network link). Also, in some cases, while two or more communications networks may be referred to, identified or shown separately, they may be implemented by a common network infrastructure.

Figure 35:
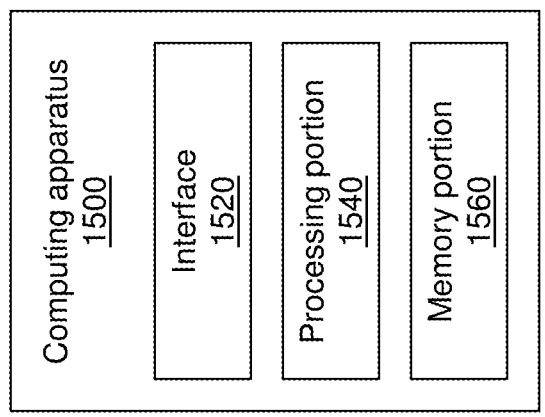
FIG. 35 shows an example of an embodiment of a computing apparatus that may implement a given component mentioned herein.

In some embodiments, as shown in FIG. 35, a given component mentioned herein (e.g., the controller 160 and/or another part of the control system 130 of the electronic cigarette 100; a component of the communication device 400, etc.) may comprise a computing apparatus 1500 comprising suitable hardware and/or software (e.g., firmware) configured to implement functionality of that given component. The computing apparatus 1500 comprises an interface 1520, a processing portion 1540, and a memory portion 1560.

The interface 1520 comprises one or more inputs and outputs allowing the computing apparatus 1500 to receive signals from and send signals to other components to which the computing apparatus 1500 is connected (i.e., directly or indirectly connected);

The processing portion 1540 comprises one or more processors for performing processing operations that implement functionality of the computing apparatus 1500. A processor of the processing portion 1540 may be a general-purpose processor executing program code stored in the memory portion 1560. Alternatively, a processor of the processing portion 1540 may be a specific-purpose processor comprising one or more preprogrammed hardware or firmware elements (e.g., application-specific integrated circuits (ASICs), electrically erasable programmable read-only memories (EEPROMs), etc.) or other related elements).

The memory portion 1560 comprises one or more memories for storing program code executed by the processing portion 1540 and/or data used during operation of the processing portion 1540. A memory of the memory portion 1560 may be a semiconductor medium (including, e.g., a solid state memory), a magnetic storage medium, an optical storage medium, and/or any other suitable type of memory. A memory of the memory portion 1560 may be read-only memory (ROM) and/or random-access memory (RAM), for example.

In some embodiments, two or more elements of the computing apparatus 1500 may be implemented by devices that are physically distinct from one another (e.g., located in a common site or in remote sites) and may be connected to one another via a bus (e.g., one or more electrical conductors or any other suitable bus) or via a communication link which may be wired, wireless, or both and which may traverse one or more networks (e.g., the Internet or any other computer network such as a local-area network (LAN) or wide-area network (WAN), a cellular network, etc.). In other embodiments, two or more elements of the computing apparatus of the vehicle 10 may be implemented by a single device.

Any feature of any embodiment discussed herein may be combined with any feature of any other embodiment discussed herein in some examples of implementation.

Certain additional elements that may be needed for operation of certain embodiments have not been described or illustrated as they are assumed to be within the purview of those of ordinary skill in the art. Moreover, certain embodiments may be free of, may lack and/or may function without one or more elements that are not specifically disclosed herein.

Although various embodiments and examples have been presented, this was for the purpose of describing, but not limiting, the invention. Various modifications and enhancements will become apparent to those of ordinary skill in the art and are within the scope of the invention.

The invention claimed is:

1. A system for controlling use of an electronic vaping device by a user, the electronic vaping device comprising an outlet and a vapor producer configured to produce vapor drawable by the user through the outlet using the user's mouth, a capability of the electronic vaping device to be vaped being disabled when the electronic vaping device is purchased by the user, the system comprising:
   an interface configured to receive information regarding the user; and
   at least one processor configured to, after the electronic vaping device is purchased by the user: process the information regarding the user to determine whether the user is allowed to vape the electronic vaping device, including by causing at least part of the information regarding the user to be verified by a third party to confirm an age of the user; and enable the capability of the electronic vaping device to be vaped if the user is allowed to vape the electronic vaping device.

2. A system for controlling use of an electronic vaping device by a user, the electronic vaping device comprising an outlet and a vapor producer configured to produce vapor drawable by the user through the outlet using the user's mouth, a capability of the electronic vaping device to be vaped being disabled when the electronic vaping device is purchased by the user, the system comprising:
   an interface configured to receive information regarding the user; and
   at least one processor configured to, after the electronic vaping device is purchased by the user: process the information regarding the user to determine whether the user is allowed to vape the electronic vaping device based on an age of the user; and enable the capability of the electronic vaping device to be vaped if the user is allowed to vape the electronic vaping device.

3. The system of claim 2, wherein: the electronic vaping device is wirelessly connectable to a communication device of the user; and the information regarding the user is provided by the communication device.

4. The system of claim 2, wherein, to process the information regarding the user to determine whether the user is allowed to vape the electronic vaping device based on the age of the user, the at least one processor is configured to cause at least part of the information regarding the user to be verified by a third party to confirm the age of the user.

5. The system of claim 4, wherein the third party is a government agency.

6. The system of claim 4, wherein the third party is a credit card company.

7. The system of claim 2, wherein the information regarding the user comprises information on a driver's license of the user.

8. The system of claim 2, wherein the information regarding the user comprises information on a credit card of the user.

9. The system of claim 2, wherein the information regarding the user comprises a biometric of the user.

10. The system of claim 2, wherein the interface is configured to receive data regarding a picture.

11. The system of claim 2, wherein the at least one processor is configured to obtain the age of the user based on the information regarding the user.

12. The system of claim 2, wherein the information regarding the user comprises the age of the user.

13. The system of claim 2, wherein the at least one processor is configured to process the information regarding the user to determine whether the user is allowed to vape the electronic vaping device based on the age of the user and a location of the electronic vaping device.

14. The system of claim 13, wherein the location of the electronic vaping device is relative to a predetermined area defined in a database.

15. The system of claim 2, wherein: the interface is configured to receive input from the user indicative of a desire of the user to disable the capability of the electronic vaping device to be vaped; the input from the user is received subsequent to the at least one processor enabling the capability of the electronic vaping device to be vaped if the user is allowed to vape the electronic vaping device; and the at least one processor is configured to disable the capability of the electronic vaping device to be vaped in response to the input from the user.

16. The system of claim 15, wherein: the input from the user is first input from the user; the interface is configured to receive second input from the user indicative of a desire of the user to enable the capability of the electronic vaping device to be vaped; the second input from the user is received subsequent to disabling of the capability of the electronic vaping device to be vaped in response to the first input from the user; and the at least one processor is configured to enable the capability of the electronic vaping device to be vaped in response to the second input from the user.

17. The system of claim 2, wherein the at least one processor is configured to cause a notification of potential unauthorized use of the electronic vaping device.

18. The system of claim 2, wherein a communication device of the user is wirelessly connectable to the electronic vaping device and comprises at least part of the interface and the at least one processor.

19. The system of claim 2, wherein a computer of an entity commercializing the electronic vaping device is separate from the electronic vaping device and comprises at least part of the interface and the at least one processor.

20. A method for controlling use of an electronic vaping device by a user, the electronic vaping device comprising an outlet and a vapor producer configured to produce vapor drawable by the user through the outlet using the user's mouth, the method comprising:
   providing the electronic vaping device to the user such that a capability of the electronic vaping device to be vaped is disabled when the electronic vaping device is purchased by the user; and
   after the electronic vaping device is purchased by the user, using a computing apparatus to: process information regarding the user to determine whether the user is allowed to vape the electronic vaping device based on an age of the user; and enable the capability of the electronic vaping device to be vaped if the user is allowed to vape the electronic vaping device.

\* \* \* \* \*